(12) United States Patent
Slayton

(10) Patent No.: US 11,717,661 B2
(45) Date of Patent: Aug. 8, 2023

(54) METHODS AND SYSTEMS FOR ULTRASOUND ASSISTED DELIVERY OF A MEDICANT TO TISSUE

(71) Applicant: Guided Therapy Systems, LLC, Mesa, AZ (US)

(72) Inventor: Michael H. Slayton, Tempe, AZ (US)

(73) Assignee: Guided Therapy Systems, LLC, Scottsdale, AZ (US)

( * ) Notice: Subject to any disclaimer, the term of this patent is extended or adjusted under 35 U.S.C. 154(b) by 0 days.

(21) Appl. No.: 15/555,913

(22) PCT Filed: Mar. 3, 2016

(86) PCT No.: PCT/US2016/020600
§ 371 (c)(1),
(2) Date: Sep. 5, 2017

(87) PCT Pub. No.: WO2016/141136
PCT Pub. Date: Sep. 9, 2016

(65) Prior Publication Data
US 2018/0043147 A1 Feb. 15, 2018

Related U.S. Application Data

(63) Continuation of application No. 14/637,237, filed on Mar. 3, 2015, now abandoned.
(Continued)

(51) Int. Cl.
*A61M 37/00* (2006.01)
*A61N 7/00* (2006.01)
*A61B 90/00* (2016.01)

(52) U.S. Cl.
CPC ... *A61M 37/0092* (2013.01); *A61B 2090/378* (2016.02); *A61M 2037/0007* (2013.01); *A61N 7/00* (2013.01); *A61N 2007/0008* (2013.01)

(58) Field of Classification Search
CPC ............... A61M 2037/0007; A61M 37/0092
See application file for complete search history.

(56) References Cited

U.S. PATENT DOCUMENTS

| 40,403 A | 10/1863 | Gray |
| 2,427,348 A | 9/1947 | Bond |

(Continued)

FOREIGN PATENT DOCUMENTS

| EP | 0344773 | 12/1989 |
| EP | 1479412 | 11/1991 |

(Continued)

OTHER PUBLICATIONS

Bommannan et al. "Sonophoresis. II. Examination of the mechanism(s) of ultrasound-enhanced transdermal drug delivery", 1992, Pharmaceutical Research, Aug; 9(8):1043-7 (Year: 1992).*

(Continued)

*Primary Examiner* — William R Carpenter
(74) *Attorney, Agent, or Firm* — GTC Law Group PC & Affiliates

(57) ABSTRACT

This disclosure provides methods and systems for ultrasound assisted delivery of a medicant to tissue. The delivery of the medicant is enhanced by the application of high intensity ultrasound pulses, which generate an intertial cavitation effect, an acoustic streaming effect, or both. This disclosure also provides methods and systems for alleviating pain or swelling associated with the application of ultrasound energy by delivering an anesthetic across a stratum corneum layer according to the methods described herein.

11 Claims, 7 Drawing Sheets

Related U.S. Application Data

(60) Provisional application No. 62/127,720, filed on Mar. 3, 2015, provisional application No. 62/127,715, filed on Mar. 3, 2015.

(56) References Cited

U.S. PATENT DOCUMENTS

| | | |
|---|---|---|
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto et al. |
| 4,166,967 A | 9/1979 | Benes et al. |
| 4,211,948 A | 7/1980 | Smith et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller et al. |
| 4,507,582 A | 3/1985 | Glenn |
| 4,513,749 A | 4/1985 | Kino et al. |
| 4,513,750 A | 4/1985 | Heyman et al. |
| 4,527,550 A | 7/1985 | Ruggera et al. |
| 4,528,979 A | 7/1985 | Marchenko et al. |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu et al. |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough et al. |
| 4,663,358 A | 5/1987 | Hyon et al. |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry et al. |
| 4,860,732 A | 8/1989 | Hasegawa et al. |
| 4,865,041 A | 9/1989 | Hassler et al. |
| 4,865,042 A | 9/1989 | Umemura et al. |
| 4,867,169 A | 9/1989 | Machida et al. |
| 4,874,562 A | 10/1989 | Hyon et al. |
| 4,875,487 A | 10/1989 | Seppi |
| 4,891,043 A | 1/1990 | Zeimer et al. |
| 4,893,624 A | 1/1990 | Lele |
| 4,896,673 A | 1/1990 | Rose et al. |
| 4,900,540 A | 2/1990 | Ryan et al. |
| 4,901,729 A | 2/1990 | Saitoh et al. |
| 4,917,096 A | 4/1990 | Englehart et al. |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry et al. |
| 4,955,365 A | 9/1990 | Fry et al. |
| 4,958,626 A | 9/1990 | Nambu et al. |
| 4,973,096 A | 11/1990 | Joyce |
| 4,976,709 A | 12/1990 | Sand |
| 4,979,501 A | 12/1990 | Valchanov et al. |
| 4,992,989 A | 2/1991 | Watanabe et al. |
| 5,012,797 A | 5/1991 | Liang et al. |
| 5,018,508 A | 5/1991 | Fry et al. |
| 5,030,874 A | 7/1991 | Saito et al. |
| 5,036,855 A | 8/1991 | Fry et al. |
| 5,040,537 A | 8/1991 | Katakura |
| 5,054,310 A | 10/1991 | Flynn |
| 5,054,470 A | 10/1991 | Fry et al. |
| 5,070,879 A | 12/1991 | Herres |
| 5,088,495 A | 2/1992 | Miyagawa |
| 5,115,814 A | 5/1992 | Griffith et al. |
| 5,117,832 A | 6/1992 | Sanghvi et al. |
| 5,123,418 A | 6/1992 | Saurel et al. |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki et al. |
| 5,158,536 A | 10/1992 | Sekins et al. |
| 5,159,931 A | 11/1992 | Pini |
| 5,163,421 A | 11/1992 | Bernstein et al. |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod et al. |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D'Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa et al. |
| 5,267,985 A | 12/1993 | Shimada et al. |
| 5,269,297 A | 12/1993 | Weng et al. |
| 5,282,797 A | 2/1994 | Chess |
| 5,295,484 A | 3/1994 | Marcus et al. |
| 5,295,486 A | 3/1994 | Wollschlager et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,348,016 A | 9/1994 | Unger et al. |
| 5,360,268 A | 11/1994 | Hayashi et al. |
| 5,370,121 A | 12/1994 | Reichenberger et al. |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |
| 5,383,917 A | 1/1995 | Desai et al. |
| 5,391,140 A | 2/1995 | Schaetzle et al. |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams, Jr. et al. |
| 5,417,216 A | 5/1995 | Tanaka |
| 5,419,327 A | 5/1995 | Rohwedder et al. |
| 5,423,220 A | 6/1995 | Finsterwald et al. |
| 5,435,311 A | 7/1995 | Umemura et al. |
| 5,438,998 A | 8/1995 | Hanafy |
| 5,458,140 A * | 8/1995 | Eppstein et al. .......... A61B 5/00 128/632 |
| 5,458,596 A | 10/1995 | Lax et al. |
| 5,460,179 A | 10/1995 | Okunuki et al. |
| 5,460,595 A | 10/1995 | Hall et al. |
| 5,469,854 A | 11/1995 | Unger et al. |

(56) References Cited

U.S. PATENT DOCUMENTS

| | | |
|---|---|---|
| 5,471,488 A | 11/1995 | Bender |
| 5,487,388 A | 1/1996 | Rello et al. |
| 5,492,126 A | 2/1996 | Hennige et al. |
| 5,496,256 A | 3/1996 | Bock et al. |
| 5,501,655 A | 3/1996 | Rolt et al. |
| 5,503,152 A | 4/1996 | Oakley et al. |
| 5,503,320 A | 4/1996 | Webster et al. |
| 5,507,790 A | 4/1996 | Weiss |
| 5,520,188 A | 5/1996 | Hennige et al. |
| 5,522,869 A | 6/1996 | Burdette et al. |
| 5,523,058 A | 6/1996 | Umemura et al. |
| 5,524,620 A | 6/1996 | Rosenschein |
| 5,524,624 A | 6/1996 | Tepper et al. |
| 5,524,625 A | 6/1996 | Okazaki et al. |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz et al. |
| 5,529,070 A | 6/1996 | Augustine et al. |
| 5,540,235 A | 7/1996 | Wilson |
| 5,558,092 A | 9/1996 | Unger et al. |
| 5,560,362 A | 10/1996 | Sliwa, Jr. et al. |
| 5,575,291 A | 11/1996 | Hayakawa et al. |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,601,526 A | 2/1997 | Chapelon et al. |
| 5,603,323 A | 2/1997 | Pflugrath et al. |
| 5,609,562 A | 3/1997 | Kaali |
| 5,615,091 A | 3/1997 | Palatnik |
| 5,617,858 A | 4/1997 | Taverna et al. |
| 5,618,275 A | 4/1997 | Bock |
| 5,620,479 A | 4/1997 | Diederich |
| 5,622,175 A | 4/1997 | Sudol et al. |
| 5,638,819 A | 6/1997 | Manwaring et al. |
| 5,643,179 A | 7/1997 | Fujimoto |
| 5,644,085 A | 7/1997 | Lorraine et al. |
| 5,647,373 A | 7/1997 | Paltieli |
| 5,655,535 A | 8/1997 | Friemel et al. |
| 5,655,538 A | 8/1997 | Lorraine et al. |
| 5,657,760 A | 8/1997 | Ying et al. |
| 5,658,328 A | 8/1997 | Johnson |
| 5,660,836 A | 8/1997 | Knowlton |
| 5,662,116 A | 9/1997 | Kondo et al. |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi et al. |
| 5,685,820 A | 11/1997 | Riek et al. |
| 5,687,737 A | 11/1997 | Branham et al. |
| 5,690,608 A | 11/1997 | Watanabe et al. |
| 5,694,936 A | 12/1997 | Fujimoto et al. |
| 5,697,897 A | 12/1997 | Buchholtz et al. |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki et al. |
| 5,727,554 A | 3/1998 | Kalend et al. |
| 5,735,280 A | 4/1998 | Sherman et al. |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa, Jr. et al. |
| 5,755,228 A | 5/1998 | Wilson et al. |
| 5,755,753 A | 5/1998 | Knowlton |
| 5,762,066 A | 6/1998 | Law et al. |
| 5,763,886 A | 6/1998 | Schulte |
| 5,769,790 A | 6/1998 | Watkins et al. |
| 5,779,644 A | 7/1998 | Eberle et al. |
| 5,792,058 A | 8/1998 | Lee et al. |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton et al. |
| 5,823,962 A | 10/1998 | Schaetzle et al. |
| 5,827,204 A | 10/1998 | Grandia et al. |
| 5,840,032 A | 11/1998 | Hatfield et al. |
| 5,844,140 A | 12/1998 | Seale |
| 5,853,367 A | 12/1998 | Chalek et al. |
| 5,869,751 A | 2/1999 | Bonin |
| 5,871,524 A | 2/1999 | Knowlton |
| 5,873,902 A | 2/1999 | Sanghvi et al. |
| 5,876,431 A | 3/1999 | Spehr et al. |
| 5,879,303 A | 3/1999 | Averkiou et al. |
| 5,882,557 A | 3/1999 | Hayakawa et al. |
| 5,891,034 A | 4/1999 | Bucholz |
| 5,899,861 A | 5/1999 | Friemel et al. |
| 5,904,659 A | 5/1999 | Duarte et al. |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder et al. |
| 5,948,011 A | 9/1999 | Knowlton |
| 5,957,844 A | 9/1999 | Dekel et al. |
| 5,957,882 A | 9/1999 | Nita et al. |
| 5,957,941 A | 9/1999 | Ream |
| 5,967,980 A | 10/1999 | Ferre et al. |
| 5,968,034 A | 10/1999 | Fullmer et al. |
| 5,971,949 A | 10/1999 | Levin et al. |
| 5,977,538 A | 11/1999 | Unger et al. |
| 5,984,882 A | 11/1999 | Rosenschein et al. |
| 5,990,598 A | 11/1999 | Sudol et al. |
| 5,997,471 A | 12/1999 | Gumb et al. |
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,016,255 A | 1/2000 | Bolan et al. |
| 6,019,724 A | 2/2000 | Gronningsaeter et al. |
| 6,022,308 A | 2/2000 | Williams |
| 6,022,327 A | 2/2000 | Chang |
| 6,036,646 A | 3/2000 | Barthe et al. |
| 6,039,048 A | 3/2000 | Silberg |
| 6,039,689 A | 3/2000 | Lizzi |
| 6,042,556 A | 3/2000 | Beach et al. |
| 6,049,159 A | 4/2000 | Barthe et al. |
| 6,050,943 A | 4/2000 | Slayton et al. |
| 6,059,727 A | 5/2000 | Fowlkes et al. |
| 6,071,239 A | 6/2000 | Cribbs et al. |
| 6,080,108 A | 6/2000 | Dunham |
| 6,083,148 A | 7/2000 | Williams |
| 6,086,535 A | 7/2000 | Ishibashi et al. |
| 6,086,580 A | 7/2000 | Mordon et al. |
| 6,090,054 A | 7/2000 | Tagishi et al. |
| 6,093,883 A | 7/2000 | Sanghvi et al. |
| 6,101,407 A | 8/2000 | Groezinger |
| 6,106,469 A | 8/2000 | Suzuki et al. |
| 6,113,558 A | 9/2000 | Rosenschein et al. |
| 6,113,559 A | 9/2000 | Klopotek |
| 6,120,452 A | 9/2000 | Barthe et al. |
| 6,123,081 A | 9/2000 | Durette |
| 6,126,619 A | 10/2000 | Peterson et al. |
| 6,135,971 A | 10/2000 | Hutchinson et al. |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura et al. |
| 6,183,426 B1 | 2/2001 | Akisada et al. |
| 6,183,502 B1 | 2/2001 | Takeuchi |

(56) References Cited

U.S. PATENT DOCUMENTS

| | | |
|---|---|---|
| 6,183,773 B1 | 2/2001 | Anderson |
| 6,190,323 B1 | 2/2001 | Dias et al. |
| 6,190,336 B1 | 2/2001 | Duarte et al. |
| 6,193,658 B1 | 2/2001 | Wendelken et al. |
| 6,210,327 B1 | 4/2001 | Brackett et al. |
| 6,213,948 B1 | 4/2001 | Barthe et al. |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 | 6/2001 | Knowlton |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao et al. |
| 6,273,864 B1 | 8/2001 | Duarte et al. |
| 6,280,402 B1 | 8/2001 | Ishibashi et al. |
| 6,287,257 B1 | 9/2001 | Matichuk |
| 6,296,619 B1 | 10/2001 | Brisken et al. |
| 6,301,989 B1 | 10/2001 | Brown et al. |
| 6,309,355 B1 | 10/2001 | Cain et al. |
| 6,311,090 B1 | 10/2001 | Knowlton |
| 6,315,741 B1 | 11/2001 | Martin et al. |
| 6,322,509 B1 | 11/2001 | Pan et al. |
| 6,322,532 B1 | 11/2001 | D'Sa et al. |
| 6,325,540 B1 | 12/2001 | Lounsberry et al. |
| 6,325,758 B1 | 12/2001 | Carol et al. |
| 6,325,769 B1 * | 12/2001 | Klopotek ............... A61N 7/00 601/2 |
| 6,325,798 B1 | 12/2001 | Edwards et al. |
| 6,338,716 B1 | 1/2002 | Hossack et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,398,753 B2 * | 6/2002 | McDaniel ............ A61B 17/20 604/22 |
| 6,405,090 B1 | 6/2002 | Knowlton |
| 6,409,720 B1 | 6/2002 | Hissong et al. |
| 6,413,216 B1 | 7/2002 | Cain et al. |
| 6,413,253 B1 | 7/2002 | Koop et al. |
| 6,413,254 B1 | 7/2002 | Hissong et al. |
| 6,419,648 B1 | 7/2002 | Vitek et al. |
| 6,423,007 B2 | 7/2002 | Lizzi et al. |
| 6,425,865 B1 | 7/2002 | Salcudean et al. |
| 6,425,867 B1 | 7/2002 | Vaezy et al. |
| 6,425,912 B1 | 7/2002 | Knowlton |
| 6,428,477 B1 | 8/2002 | Mason |
| 6,428,532 B1 | 8/2002 | Doukas et al. |
| 6,430,446 B1 | 8/2002 | Knowlton |
| 6,432,057 B1 | 8/2002 | Mazess et al. |
| 6,432,067 B1 | 8/2002 | Martin et al. |
| 6,432,101 B1 | 8/2002 | Weber et al. |
| 6,436,061 B1 | 8/2002 | Costantino |
| 6,438,424 B1 | 8/2002 | Knowlton |
| 6,440,071 B1 | 8/2002 | Slayton et al. |
| 6,440,121 B1 | 8/2002 | Weber et al. |
| 6,443,914 B1 | 9/2002 | Costantino |
| 6,453,202 B1 | 9/2002 | Knowlton |
| 6,461,378 B1 | 10/2002 | Knowlton |
| 6,470,216 B1 | 10/2002 | Knowlton |
| 6,488,626 B1 | 12/2002 | Lizzi et al. |
| 6,491,657 B2 | 12/2002 | Rowe et al. |
| 6,500,121 B1 | 12/2002 | Slayton et al. |
| 6,500,141 B1 | 12/2002 | Irion et al. |
| 6,508,774 B1 | 1/2003 | Acker et al. |
| 6,511,427 B1 | 1/2003 | Sliwa, Jr. et al. |
| 6,511,428 B1 | 1/2003 | Azuma et al. |
| 6,514,244 B2 | 2/2003 | Pope et al. |
| 6,517,484 B1 | 2/2003 | Wilk et al. |
| 6,524,250 B1 | 2/2003 | Weber et al. |
| 6,540,679 B2 | 4/2003 | Slayton et al. |
| 6,540,685 B1 | 4/2003 | Rhoads et al. |
| 6,540,700 B1 | 4/2003 | Fujimoto et al. |
| 6,554,771 B1 | 4/2003 | Buil et al. |
| 6,569,099 B1 | 5/2003 | Babaev |
| 6,569,108 B2 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong et al. |
| 6,599,256 B1 | 7/2003 | Acker et al. |
| 6,607,498 B2 | 8/2003 | Eshel |
| 6,618,620 B1 | 9/2003 | Freundlich et al. |
| 6,623,430 B1 | 9/2003 | Slayton et al. |
| 6,626,854 B2 | 9/2003 | Friedman et al. |
| 6,626,855 B1 | 9/2003 | Weng et al. |
| 6,638,226 B2 | 10/2003 | He et al. |
| 6,645,162 B2 | 11/2003 | Friedman et al. |
| 6,662,054 B2 | 12/2003 | Kreindel et al. |
| 6,663,627 B2 | 12/2003 | Francischelli et al. |
| 6,665,806 B1 | 12/2003 | Shimizu |
| 6,666,835 B2 | 12/2003 | Martin et al. |
| 6,669,638 B1 | 12/2003 | Miller et al. |
| 6,685,640 B1 | 2/2004 | Fry et al. |
| 6,692,450 B1 | 2/2004 | Coleman |
| 6,699,237 B2 | 3/2004 | Weber et al. |
| 6,716,184 B2 | 4/2004 | Vaezy et al. |
| 6,719,449 B1 | 4/2004 | Laugham, Jr. et al. |
| 6,719,694 B2 | 4/2004 | Weng et al. |
| 6,726,627 B1 | 4/2004 | Lizzi et al. |
| 6,733,449 B1 | 5/2004 | Krishnamurthy et al. |
| 6,749,624 B2 | 6/2004 | Knowlton |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,882,884 B1 | 4/2005 | Mosk et al. |
| 6,887,239 B2 | 5/2005 | Elstrom et al. |
| 6,889,089 B2 | 5/2005 | Behl et al. |
| 6,896,657 B2 | 5/2005 | Willis |
| 6,902,536 B2 | 6/2005 | Manna et al. |
| 6,905,466 B2 | 6/2005 | Salgo et al. |
| 6,918,907 B2 | 7/2005 | Kelly et al. |
| 6,920,883 B2 | 7/2005 | Bessette et al. |
| 6,921,371 B2 | 7/2005 | Wilson |
| 6,932,771 B2 | 8/2005 | Whitmore et al. |
| 6,932,814 B2 | 8/2005 | Wood |
| 6,936,044 B2 | 8/2005 | McDaniel |
| 6,936,046 B2 | 8/2005 | Hissong et al. |
| 6,945,937 B2 | 9/2005 | Culp et al. |
| 6,948,843 B2 | 9/2005 | Laugham, Jr. et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood et al. |
| 6,976,492 B2 | 12/2005 | Ingle et al. |
| 6,992,305 B2 | 1/2006 | Maezawa et al. |
| 6,997,923 B2 | 2/2006 | Anderson et al. |
| 7,006,874 B2 | 2/2006 | Knowlton et al. |
| 7,020,528 B2 | 3/2006 | Neev |
| 7,022,089 B2 | 4/2006 | Ooba et al. |
| 7,058,440 B2 | 6/2006 | Heuscher et al. |
| 7,063,666 B2 | 6/2006 | Weng et al. |
| 7,070,565 B2 * | 7/2006 | Vaezy et al. ........... A61B 8/14 600/459 |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton et al. |
| 7,122,029 B2 | 10/2006 | Koop et al. |
| 7,142,905 B2 | 11/2006 | Slayton et al. |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton et al. |

(56) References Cited

U.S. PATENT DOCUMENTS

| | | |
|---|---|---|
| 7,235,592 B2 | 6/2007 | Muratoglu et al. |
| 7,258,674 B2 | 8/2007 | Cribbs et al. |
| 7,273,459 B2 | 9/2007 | Desilets et al. |
| 7,294,125 B2 | 11/2007 | Phalen et al. |
| 7,297,117 B2 | 11/2007 | Trucco et al. |
| 7,303,555 B2 | 12/2007 | Makin et al. |
| 7,327,071 B2 | 2/2008 | Nishiyama et al. |
| 7,331,951 B2 | 2/2008 | Eshel et al. |
| 7,332,985 B2 | 2/2008 | Larson, III et al. |
| 7,347,855 B2 | 3/2008 | Eshel et al. |
| 7,393,325 B2 | 7/2008 | Barthe et al. |
| 7,398,116 B2 | 7/2008 | Edwards |
| 7,399,279 B2 | 7/2008 | Abend et al. |
| 7,491,171 B2 | 2/2009 | Barthe et al. |
| 7,510,536 B2 | 3/2009 | Foley et al. |
| 7,530,356 B2 | 5/2009 | Slayton et al. |
| 7,530,958 B2 * | 5/2009 | Slayton ............... A61H 23/0245 601/2 |
| 7,571,336 B2 | 8/2009 | Barthe et al. |
| 7,601,120 B2 | 10/2009 | Moilanen et al. |
| 7,615,015 B2 | 11/2009 | Coleman |
| 7,615,016 B2 | 11/2009 | Barthe et al. |
| 7,686,763 B2 | 3/2010 | Vaezy et al. |
| 7,695,437 B2 | 4/2010 | Quistgaard et al. |
| 7,758,524 B2 | 7/2010 | Barthe et al. |
| 7,789,841 B2 | 9/2010 | Huckle et al. |
| 7,824,348 B2 | 11/2010 | Barthe et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,914,453 B2 | 3/2011 | Slayton et al. |
| 7,914,469 B2 | 3/2011 | Torbati |
| 7,931,611 B2 | 4/2011 | Novak et al. |
| 7,955,281 B2 | 6/2011 | Pedersen et al. |
| 7,967,764 B2 | 6/2011 | Lidgren et al. |
| 7,967,839 B2 | 6/2011 | Flock et al. |
| 8,057,389 B2 | 11/2011 | Barthe et al. |
| 8,057,465 B2 | 11/2011 | Sliwa, Jr. et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,166,332 B2 | 4/2012 | Barthe et al. |
| 8,197,409 B2 | 6/2012 | Foley et al. |
| 8,206,299 B2 | 6/2012 | Foley et al. |
| 8,211,017 B2 | 7/2012 | Foley et al. |
| 8,262,591 B2 | 9/2012 | Pedersen et al. |
| 8,273,037 B2 | 9/2012 | Kreindel et al. |
| 8,282,554 B2 | 10/2012 | Makin et al. |
| 8,333,700 B1 | 12/2012 | Barthe et al. |
| 8,366,622 B2 | 2/2013 | Slayton et al. |
| 8,409,097 B2 | 4/2013 | Slayton et al. |
| 8,444,562 B2 | 5/2013 | Barthe et al. |
| 8,480,585 B2 | 7/2013 | Slayton et al. |
| 8,506,486 B2 | 8/2013 | Slayton et al. |
| 8,523,775 B2 | 9/2013 | Barthe et al. |
| 8,535,228 B2 | 9/2013 | Slayton et al. |
| 8,585,618 B2 | 11/2013 | Hunziker et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 2001/0009997 A1 | 7/2001 | Pope |
| 2001/0009999 A1 | 7/2001 | Kaufman |
| 2001/0014780 A1 | 8/2001 | Martin |
| 2001/0014819 A1 | 8/2001 | Ingle et al. |
| 2001/0031922 A1 | 10/2001 | Weng et al. |
| 2001/0039380 A1 | 11/2001 | Larson et al. |
| 2001/0041880 A1 | 11/2001 | Brisken et al. |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0052550 A1 | 5/2002 | Madsen et al. |
| 2002/0055702 A1 | 5/2002 | Atala et al. |
| 2002/0062077 A1 | 5/2002 | Emmenegger et al. |
| 2002/0062142 A1 | 5/2002 | Knowlton |
| 2002/0072691 A1 | 6/2002 | Thompson et al. |
| 2002/0082528 A1 | 6/2002 | Friedman et al. |
| 2002/0082529 A1 | 6/2002 | Suorsa et al. |
| 2002/0082589 A1 | 6/2002 | Friedman et al. |
| 2002/0087080 A1 | 7/2002 | Slayton |
| 2002/0095143 A1 | 7/2002 | Key |
| 2002/0099094 A1 | 7/2002 | Anderson |
| 2002/0115917 A1 | 8/2002 | Honda et al. |
| 2002/0128592 A1 * | 9/2002 | Eshel ................... A61B 17/20 604/22 |
| 2002/0128648 A1 | 9/2002 | Weber et al. |
| 2002/0143252 A1 | 10/2002 | Dunne et al. |
| 2002/0156400 A1 | 10/2002 | Babaev |
| 2002/0161357 A1 | 10/2002 | Anderson et al. |
| 2002/0165529 A1 | 11/2002 | Danek |
| 2002/0168049 A1 | 11/2002 | Schriever et al. |
| 2002/0169394 A1 * | 11/2002 | Eppstein .......... A61B 5/150083 600/573 |
| 2002/0169442 A1 | 11/2002 | Neev |
| 2002/0173721 A1 | 11/2002 | Grunwald et al. |
| 2002/0193784 A1 | 12/2002 | McHale et al. |
| 2002/0193831 A1 | 12/2002 | Smith, III |
| 2003/0009153 A1 * | 1/2003 | Brisken ............ A61M 37/0092 604/890.1 |
| 2003/0014039 A1 | 1/2003 | Barzell et al. |
| 2003/0018255 A1 | 1/2003 | Martin et al. |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton |
| 2003/0040739 A1 | 2/2003 | Koop |
| 2003/0050678 A1 | 3/2003 | Sierra et al. |
| 2003/0055417 A1 | 3/2003 | Truckai et al. |
| 2003/0060736 A1 | 3/2003 | Martin et al. |
| 2003/0065313 A1 | 4/2003 | Koop et al. |
| 2003/0074023 A1 | 4/2003 | Kaplan et al. |
| 2003/0083536 A1 | 5/2003 | Eshel et al. |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0100846 A1 | 5/2003 | Custer |
| 2003/0125629 A1 | 7/2003 | Ustuner |
| 2003/0139790 A1 | 7/2003 | Ingle et al. |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi et al. |
| 2003/0200481 A1 | 10/2003 | Stanley |
| 2003/0212129 A1 | 11/2003 | Liu et al. |
| 2003/0212351 A1 | 11/2003 | Hissong et al. |
| 2003/0212393 A1 | 11/2003 | Knowlton et al. |
| 2003/0216795 A1 | 11/2003 | Harth et al. |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton et al. |
| 2004/0001809 A1 | 1/2004 | Brisker et al. |
| 2004/0002705 A1 | 1/2004 | Knowlton et al. |
| 2004/0010222 A1 | 1/2004 | Nunomura et al. |
| 2004/0015106 A1 | 1/2004 | Coleman |
| 2004/0030227 A1 | 2/2004 | Littrup et al. |
| 2004/0039312 A1 | 2/2004 | Hillstead et al. |
| 2004/0039418 A1 | 2/2004 | Elstrom et al. |
| 2004/0041563 A1 | 3/2004 | Lewin |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Simske |

(56) References Cited

U.S. PATENT DOCUMENTS

| | | |
|---|---|---|
| 2004/0059266 A1 | 3/2004 | Fry et al. |
| 2004/0068186 A1 | 4/2004 | Ishida et al. |
| 2004/0073079 A1 | 4/2004 | Altshuler et al. |
| 2004/0073113 A1 | 4/2004 | Salgo et al. |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger et al. |
| 2004/0082859 A1 | 4/2004 | Schaer |
| 2004/0102697 A1 | 5/2004 | Evron |
| 2004/0105559 A1 | 6/2004 | Aylward et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey, III |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets et al. |
| 2004/0249318 A1 | 12/2004 | Tanaka |
| 2004/0254620 A1 | 12/2004 | Lacoste et al. |
| 2004/0267252 A1 | 12/2004 | Washington et al. |
| 2005/0033201 A1 | 2/2005 | Takahashi et al. |
| 2005/0033316 A1 | 2/2005 | Kertz |
| 2005/0038340 A1 | 2/2005 | Vaezy et al. |
| 2005/0055073 A1 | 3/2005 | Weber |
| 2005/0061834 A1 | 3/2005 | Garcia et al. |
| 2005/0070961 A1 | 3/2005 | Maki et al. |
| 2005/0074407 A1 | 4/2005 | Smith |
| 2005/0080469 A1 | 4/2005 | Larson et al. |
| 2005/0091770 A1 | 5/2005 | Mourad et al. |
| 2005/0096542 A1 | 5/2005 | Weng et al. |
| 2005/0104690 A1 | 5/2005 | Larson, III et al. |
| 2005/0113689 A1 | 5/2005 | Gritzky |
| 2005/0134314 A1 | 6/2005 | Prather et al. |
| 2005/0137656 A1 | 6/2005 | Malak |
| 2005/0143677 A1 | 6/2005 | Young et al. |
| 2005/0154313 A1 | 7/2005 | Desilets et al. |
| 2005/0154314 A1 | 7/2005 | Quistgaard |
| 2005/0154332 A1 | 7/2005 | Zanelli et al. |
| 2005/0154431 A1 | 7/2005 | Quistgaard et al. |
| 2005/0187495 A1 | 8/2005 | Quistgaard et al. |
| 2005/0191252 A1 | 9/2005 | Mitsui |
| 2005/0193451 A1 | 9/2005 | Quistgaard et al. |
| 2005/0197681 A1 | 9/2005 | Barolet et al. |
| 2005/0228281 A1 | 10/2005 | Nefos |
| 2005/0240170 A1 | 10/2005 | Zhang et al. |
| 2005/0251120 A1 | 11/2005 | Anderson et al. |
| 2005/0256406 A1 | 11/2005 | Barthe |
| 2005/0261584 A1 | 11/2005 | Eshel et al. |
| 2005/0261585 A1 | 11/2005 | Makin |
| 2005/0267454 A1 | 12/2005 | Hissong et al. |
| 2005/0288748 A1 | 12/2005 | Li et al. |
| 2006/0004306 A1 | 1/2006 | Altshuler et al. |
| 2006/0020260 A1 | 1/2006 | Dover et al. |
| 2006/0025756 A1 | 2/2006 | Francischelli et al. |
| 2006/0042201 A1 | 3/2006 | Curry |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0058664 A1 * | 4/2006 | Barthe et al. ............ A61B 8/12 600/439 |
| 2006/0074309 A1 | 4/2006 | Bonnefous |
| 2006/0074313 A1 | 4/2006 | Slayton |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin et al. |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya et al. |
| 2006/0111744 A1 | 5/2006 | Makin et al. |
| 2006/0116583 A1 | 6/2006 | Ogasawara et al. |
| 2006/0116671 A1 | 6/2006 | Slayton et al. |
| 2006/0122508 A1 | 6/2006 | Slayton et al. |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra et al. |
| 2006/0229514 A1 | 10/2006 | Wiener |
| 2006/0241440 A1 | 10/2006 | Eshel et al. |
| 2006/0241442 A1 | 10/2006 | Barthe |
| 2006/0241470 A1 | 10/2006 | Novak et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0032784 A1 | 2/2007 | Gliklich et al. |
| 2007/0035201 A1 | 2/2007 | Desilets et al. |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0055179 A1 | 3/2007 | Deem |
| 2007/0065420 A1 | 3/2007 | Johnson |
| 2007/0078290 A1 * | 4/2007 | Esenaliev ................ A61N 7/00 600/1 |
| 2007/0083120 A1 | 4/2007 | Cain et al. |
| 2007/0087060 A1 | 4/2007 | Dietrich et al. |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0208253 A1 | 9/2007 | Slayton |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg et al. |
| 2007/0239079 A1 | 10/2007 | Manstein et al. |
| 2007/0239142 A1 | 10/2007 | Altshuler et al. |
| 2008/0009885 A1 * | 1/2008 | Del Giglio ............ A61B 17/22 606/128 |
| 2008/0027328 A1 | 1/2008 | Klopotek et al. |
| 2008/0039724 A1 | 2/2008 | Seip et al. |
| 2008/0071255 A1 | 3/2008 | Barthe et al. |
| 2008/0086054 A1 | 4/2008 | Slayton et al. |
| 2008/0097253 A1 | 4/2008 | Pedersen et al. |
| 2008/0139974 A1 | 6/2008 | Da Silva |
| 2008/0146970 A1 | 6/2008 | Litman et al. |
| 2008/0167556 A1 | 7/2008 | Thompson et al. |
| 2008/0183077 A1 | 7/2008 | Moreau-Gobard et al. |
| 2008/0188745 A1 | 8/2008 | Chen et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0221491 A1 | 9/2008 | Slayton et al. |
| 2008/0223379 A1 | 9/2008 | Stuker et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton et al. |
| 2008/0294073 A1 | 11/2008 | Barthe |
| 2008/0319356 A1 | 12/2008 | Cain et al. |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0171252 A1 | 7/2009 | Bockenstedt et al. |
| 2009/0177122 A1 | 7/2009 | Peterson |
| 2009/0177123 A1 | 7/2009 | Peterson |
| 2009/0182231 A1 | 7/2009 | Barthe et al. |
| 2009/0216159 A1 | 8/2009 | Slayton et al. |

(56) References Cited

U.S. PATENT DOCUMENTS

| | | |
|---|---|---|
| 2009/0226424 A1 | 9/2009 | Hsu |
| 2009/0227910 A1 | 9/2009 | Pedersen et al. |
| 2009/0253988 A1 | 10/2009 | Slayton et al. |
| 2009/0299175 A1 | 12/2009 | Bernstein et al. |
| 2009/0318909 A1 | 12/2009 | DeBenedictis et al. |
| 2010/0011236 A1 | 1/2010 | Barthe |
| 2010/0022919 A1 | 1/2010 | Peterson |
| 2010/0022922 A1 | 1/2010 | Barthe |
| 2010/0042020 A1 | 2/2010 | Ben-Ezra |
| 2010/0049178 A1 | 2/2010 | Deem et al. |
| 2010/0063422 A1 | 3/2010 | Hynynen et al. |
| 2010/0130891 A1 | 5/2010 | Taggart et al. |
| 2010/0160782 A1 | 6/2010 | Slayton |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe |
| 2010/0280420 A1 | 11/2010 | Barthe |
| 2010/0286518 A1 | 11/2010 | Lee et al. |
| 2011/0040171 A1 | 2/2011 | Foley et al. |
| 2011/0040190 A1 | 2/2011 | Jahnke et al. |
| 2011/0087099 A1 | 4/2011 | Eshel et al. |
| 2011/0087255 A1 | 4/2011 | McCormack et al. |
| 2011/0112405 A1 | 5/2011 | Barthe et al. |
| 2011/0178444 A1 | 7/2011 | Slayton |
| 2011/0190745 A1 | 8/2011 | Uebelhoer et al. |
| 2011/0264012 A1 | 10/2011 | Lautzenhiser et al. |
| 2012/0004549 A1 | 1/2012 | Barthe |
| 2012/0016239 A1 | 1/2012 | Barthe et al. |
| 2012/0029353 A1 | 2/2012 | Slayton et al. |
| 2012/0035475 A1 | 2/2012 | Barthe et al. |
| 2012/0035476 A1 | 2/2012 | Barthe et al. |
| 2012/0046547 A1 | 2/2012 | Barthe et al. |
| 2012/0053458 A1 | 3/2012 | Barthe et al. |
| 2012/0111339 A1 | 5/2012 | Barthe |
| 2012/0143056 A1 | 6/2012 | Slayton et al. |
| 2012/0165668 A1 | 6/2012 | Slayton et al. |
| 2012/0165848 A1 | 6/2012 | Slayton et al. |
| 2012/0197120 A1 | 8/2012 | Makin |
| 2012/0197121 A1 | 8/2012 | Slayton et al. |
| 2012/0215105 A1 | 8/2012 | Slayton |
| 2012/0271167 A1* | 10/2012 | Holland ............ A61M 37/0092 600/439 |
| 2012/0271294 A1 | 10/2012 | Barthe |
| 2012/0296240 A1 | 11/2012 | Azhari et al. |
| 2012/0316426 A1 | 12/2012 | Foley et al. |
| 2012/0330197 A1 | 12/2012 | Makin et al. |
| 2012/0330222 A1 | 12/2012 | Barthe |
| 2012/0330223 A1 | 12/2012 | Makin |
| 2013/0012755 A1 | 1/2013 | Slayton |
| 2013/0012816 A1 | 1/2013 | Slayton et al. |
| 2013/0012838 A1 | 1/2013 | Jaeger |
| 2013/0012842 A1 | 1/2013 | Barthe |
| 2013/0018286 A1 | 1/2013 | Slayton |
| 2013/0046209 A1 | 2/2013 | Slayton et al. |
| 2013/0066208 A1 | 3/2013 | Barthe et al. |
| 2013/0066237 A1 | 3/2013 | Smotrich et al. |
| 2013/0072826 A1 | 3/2013 | Slayton |
| 2013/0096471 A1 | 4/2013 | Slayton et al. |
| 2013/0190659 A1 | 7/2013 | Slayton |
| 2013/0211258 A1 | 8/2013 | Barthe et al. |
| 2013/0281853 A1 | 10/2013 | Slayton |
| 2013/0281891 A1 | 10/2013 | Slayton |
| 2013/0296697 A1 | 11/2013 | Slayton et al. |
| 2013/0296700 A1 | 11/2013 | Slayton |
| 2013/0303904 A1 | 11/2013 | Barthe et al. |
| 2013/0303905 A1 | 11/2013 | Barthe et al. |
| 2013/0310863 A1 | 11/2013 | Barthe |
| 2014/0082907 A1 | 3/2014 | Barthe |
| 2014/0142430 A1 | 5/2014 | Slayton |
| 2014/0148834 A1 | 5/2014 | Barthe et al. |
| 2014/0180174 A1 | 6/2014 | Slayton |
| 2014/0187944 A1 | 7/2014 | Slayton et al. |
| 2014/0188015 A1 | 7/2014 | Slayton et al. |
| 2014/0188145 A1 | 7/2014 | Slayton et al. |

FOREIGN PATENT DOCUMENTS

| | | |
|---|---|---|
| EP | 0473553 | 4/1992 |
| EP | 0661029 | 7/1995 |
| EP | 1050322 | 11/2000 |
| EP | 1234566 | 8/2002 |
| EP | 1262160 | 12/2002 |
| EP | 1374944 | 1/2004 |
| GB | 2113099 | 8/1983 |
| WO | 1996025888 | 8/1996 |
| WO | 1996039079 | 12/1996 |
| WO | 1997035518 | 10/1997 |
| WO | 1998032379 | 7/1998 |
| WO | 1999033520 | 7/1999 |
| WO | 1999049788 | 10/1999 |
| WO | 2000006032 | 2/2000 |
| WO | 2000015300 | 3/2000 |
| WO | 2000021612 | 4/2000 |
| WO | 2000048518 | 8/2000 |
| WO | 2000053113 | 9/2000 |
| WO | 2001082777 | 11/2001 |
| WO | 2001082778 | 11/2001 |
| WO | 2001087161 | 11/2001 |
| WO | 2002009813 | 2/2002 |
| WO | 2002024050 | 3/2002 |
| WO | 2002092168 | 11/2002 |
| WO | 03053266 | 7/2003 |
| WO | 2003065347 | 8/2003 |
| WO | 2003070105 | 8/2003 |
| WO | 2003077833 | 8/2003 |
| WO | 2003086215 | 10/2003 |
| WO | 2003096883 | 11/2003 |
| WO | 2003099177 | 12/2003 |
| WO | 2003101530 | 12/2003 |
| WO | 2004000116 | 12/2003 |
| WO | 2004080147 | 9/2004 |
| WO | 2004110558 | 12/2004 |
| WO | 2005011804 | 2/2005 |
| WO | 2005051455 | 6/2005 |
| WO | 2005065408 | 7/2005 |
| WO | 2005090978 | 9/2005 |
| WO | 2006036870 | 4/2006 |
| WO | 2006042163 | 4/2006 |
| WO | 2006042168 | 4/2006 |
| WO | 2006042201 | 4/2006 |
| WO | 2006065671 | 6/2006 |
| WO | 2006082573 | 8/2006 |
| WO | 2007067563 | 6/2007 |
| WO | 2008024923 | 2/2008 |
| WO | 2008036622 | 3/2008 |
| WO | 2009013729 | 1/2009 |
| WO | 2009149390 | 12/2009 |
| WO | 2010077980 | 7/2010 |
| WO | 2001028623 | 4/2011 |
| WO | 2014055708 | 4/2014 |

OTHER PUBLICATIONS

Mitragotri et al. "A mechanistic study of ultrasonically-enhanced transdermal drug delivery", 1995, Journal of Pharmaceutical Sciences. Jun. 84(6):697-706 (Year: 1995).*

Chan et al. "Safety Study of Transcutaneous Focused Ultrasound for Non-lnvasive Skin Tightening in Asians", 2011, Lasers in Surgery and Medicine 43: 366-375 (Year: 2011).*

Alam et al. "Ultrasound Tightening of Facial and Neck Skin: A Rater-Blinded Prospective Cohort Study", 2009, The Journal of the American Academy of Dermatology, vol. 62, Iss. 2, p. 262-269 (Year: 2009).*

Singer at al. "Low-Frequency Sonophoresis: Pathologic and Thermal Effects in Dogs" 1998, The Academic Emergency Medicine. vol. 5, Iss. 1, p. 35-39 (Year: 1998).*

Tezel et al. "Interactions of Inertial Cavitation Bubbles with Stratum Corneum Lipid Bilayers during Low-Frequency Sonophoresis", 2003, Biophysical Journal vol. 85, 3502-3512 (Year: 2003).*

Paliwal et al. "Ultrasound-Induced Cavitation: Applications in Drug and Gene Delivery", 2006. Expert Opinion on Drug Delivery, #:6, 713-726 (Year: 2006).*

(56) References Cited

OTHER PUBLICATIONS

Alster, T. S., et al., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.
Arthur et al., "Non-invasive estimation of hyperthermia temperatures with ultrasound," Int. J_ Hyperthermia, Sep. 2005, 21(6), pp. 589-600.
Barthe et al., "Ultrasound therapy system and ablation results utilizing miniature imaging/therapy arrays," Ultrasonics Symposium, 2004 IEEE, Aug. 23, 2004, pp. 1792-1795, vol. 3.
Calderhead et al., One Mechanism Behind LED Photo-Therapy For Wound Healing and Skin Rejuvenation: Key Role of the Mast Cell, Laser Therapy, 2008, 17(3): 141-148.
Campbell, B. J., et al. "Systemic absorption of topical lidocaine in normal volunteers, patients with post herpetic neuralgia, and patients with acute herpes zoster." Journal of pharmaceutical sciences 91.5 (2002): 1343-1350.
Chen. L. et al. ""Effect of Blood Perfusion on the ablation of liver perenchyma with high intensity focused ultrasound,"" Phys. Med. Biol; 38:1661-1673; 1993b.
Church CC, et al. "A theoretical study of inertial cavitation from acoustic radiation force impulse imaging and implications for the mechanical index." Ultrasound in medicine & biology 41.2 (2015): 472-485.
Coon, J. et al., "Protein identification using sequential ion/ion reactions and tandem mass spectometry" Proceedings of the National Academy of Sciences of the USA, vol. 102, No. 27, Jul. 5, 2005, pp. 9463-9468.
European Examination Report in related Application No. 05808908.7 dated Jun. 29, 2009.
European Examination Report in related Application No. 05810308.6 dated Jun. 29, 2009.
European Examination Report in related Application No. 09835856.7 dated Apr. 11, 2014.
European Examination Report in related Application No. 10185100.4 dated Jan. 6, 2014.
European Examination Report in related Application No. 10185120.2 dated Jan. 22, 2014.
Written Opinion dated Aug. 12, 2008 for PCT/US2008/062930.
Corry, P. M., et al., "Human Cancer Treatment with Ultrasound", IEEE Transactions on Sonics and Ultrasonics, vol. SU-31, No. 5, Sep. 1984, pp. 444,456.
Damianou et al., Application of the Thermal Dose Concept for Predicting the Necrosed Tissue Volume During Ultrasound Surgery, 1993 IEEE Ultrasound Symposium, pp. 1199-1202.
Daum et al., "Design and Evaluation of a Feedback Based Phased Array System for Ultrasound Surgery," IEEE Transactions on Ultrasonics, Feroelectronics, and Frequency Control, vol. 45, No. 2, Mar. 1998, pp. 431-438.
Davis, B. J., et al., "An Acoustic Phase Shift Technique for the Non-lnvasive Measurement of Temperature Changes in Tissues", 1985 Ultrasonics Symposium, pp. 921-924.
Decision of the Korean Intellectual Property Tribunal dated Jun. 28, 2013 regarding Korean Patent No. 10-1142108, which is related to the pending application and/or an application identified in the Table on the pp. 2-5 of the information Disclosure Statement herein (English translation, English translation certification, and Korean decision included).
European Patent Office, Examination Report, EP 05798870.1, Oct. 20, 2014, 5 pages.
European Patent Office, Examination Report, EP 07814933.3, Aug. 5, 2014, 5 pages.
European Patent Office, Examination Report, EP 10185112.9, Oct. 24, 2014, 5 pages.
European Patent Office, Examination Report, EP 10185117.8, Oct. 24, 2014, 5 pages.
European Patent Office, Examination Report, EP 10185120.2, Oct. 24, 2014, 4 pages.

European Patent Office. Examination Report. EP 10185100.4. Oct. 24, 2014, 4 pages.
Fry, W.J. et al., "Production of Focal Destructive Lesions in the Central Nervous System with Ultrasound," J. Neurosurg., 11:471-478; 1954.
Gliklich et al, "Clinical Pilot Study of Intense Ultrasound Therapy to Deep Dermal Facial Skin and Subcutaneous Tissues," Arch Facial Plastic Surgery, Mar. 1, 2007, vol. 9, No. 1.
Haar, G.R. et al., "Tissue Destruction with Focused Ultrasound in Vivo," Eur. Ural. 23 (suppl. 1):8-11; 1993.
Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.
Hassan et al., "Structure and Morphology of Freeze/Thawed PVA Hydrogels," Macromolecules, Mar. 11, 2000, pp. 2472-2479, vol. 33, No. 7.
Husseini et al, "Investigating the mechanism of acoustically activated uptake of drugs from Pluronic micelles," BMC Cancer 2002, 2:20, Aug. 30, 2002, pp. 1-6.
Husseini et al, "The Role of Cavitation in Acoustically Activated Drug Delivery," J_Control Release, Oct. 3, 2005, pp. 253-261, vol. 107(2).
International Preliminary Report on Patentability for International application No. PCT/US2008/062930 dated Nov. 19, 2009.
International Preliminary Report on Patentability in Application No. PCT/US2011/001366 dated Feb. 14, 2013.
International Search Report and Written Opinion dated Jan. 23, 2014 in Application No. PCT/US2012/046122.
International Search Report and Written Opinion dated Jan. 23, 2014 in Application No. PCT/US2012/046123.
International Search Report and Written Opinion dated Jan. 28, 2013 in Application No. PCT/US2012/046125.
International Search Report and Written Opinion dated Feb. 14, 2013 in Application No. PCT/US2011/001361.
International Search Report and Written Opinion dated Feb. 14, 2013 in Application No. PCT/US2011/001362.
International Search Report and Written Opinion dated Feb. 14, 2013 in Application No. PCT/US2011/001366.
International Search Report and Written Opinion dated Feb. 14, 2013 in Application No. PCT/US2011/001367.
International Search Report and Written Opinion dated Sep. 28, 2012 in Application No. PCT/US2012/046327.
International Searching Authority, International Search Report and Written Opinion for application PCT/US2016/020600, dated May 18, 2016.
Jeffers et al., "Evaluation of the Effect of Cavitation Activity on Drug-Ultrasound Synergisms," 1993 IEEE Ultrasonics Symposium, pp. 925-928.
Jenne, J., et al., "Temperature Mapping for High Energy US-Therapy", 1994 Ultrasonics Symposium, pp. 1879-1882.
Johnson, S.A., et al., "Non-lntrusive Measurement of Microwave and Ultrasound-Induced Hyperthermia by Acoustic temperature Tomography", Ultrasonics Symposium Proceedings, pp. 977-982. 1977.
Madersbacher, S et al., "Tissue Ablation in Bening Prostatic Hyperplasia with High Intensity Focused Ultrasound," Dur. Ural., 23 (suppl. 1):39-43; 1993.
Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.
Makin et al, "Conformal Bulk Ablation and Therapy Monitoring Using Intracorporeal Image-Treat Ultrasound Arrays," 4th International Symposium on Theraputic Ultrasound, Sep. 19, 2004.
Makin et al, "Miniaturized Ultrasound Arrays for Interstitial Ablation and Imaging," Ultrasound Med. Biol. 2005, Nov. 1, 2005, pp. 1539-1550, vol. 31(11).
Manohar et al, "Photoacoustic mammography laboratory prototype: imaging of breast tissue phantoms," Journal of Biomedical Optics, Nov./Dec. 2004, pp. 1172-1181, vol. 9, No. 6.

(56) References Cited

OTHER PUBLICATIONS

Mast et al, "Bulk Ablation of Soft Tissue with Intense Ultrasound: Modeling and Experiments," J_Acoust. Soc. Am., Oct. 1, 2005, pp. 2715-2724, vol. 118(4).

Mitragotri, S.; "Healing sound: the use of ultrasound in drug delivery and other therapeutic applications," Nature Reviews; Drug Delivery, pp. 255-260, vol. 4. 2005.

Paradossi et al., "Poly(vinyl alcohol) as versatile biomaterial for potential biomedical applications," Journal of Materials Science: Materials in Medicine, 2003, pp. 687-691, vol. 14.

PCT International Search Report and Written Opinion, PCT/US2014/030779, Sep. 1, 2014, 8 pages.

Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.

Righetti et al, "Elastographic Characterization of HIFU-lnduced Lesions in Canine Livers," 1999, Ultrasound in Med & Bio, vol. 25, No. 7, pp. 1099-1113.

Saad et al., "Ultrasound-Enhanced Effects of Adriamycin Against Murine Tumors," Ultrasound in Med. & Biol. vol. 18, No. 8, pp. 715-723 (1992).

Sanghvi, N.T., et al., "Transrectal Ablation of Prostrate Tissue Using Focused Ultrasound," 1993 Ultrasonics Symposium, IEEE, pp. 1207-1210.

Sassen, S., "ATI's R520 architecture, the new king of the hill?" http://www.hardwareanalysis.com/content/article/1813, Sep. 16, 2005, 2 pages.

Seip, R., et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.

Seip, R.. et al. "Noninvasive Detection of Thermal Effects Due to Highly Focused Ultrasonic Fiels," IEEE Symposium, pp. 1229-1232, vol. 2, Oct. 3-Nov. 1993.

Simon et al., "Applications of Lipid-Coated Microbubble Ultrasonic Contrast to Tumor Therapy," Ultrasound in Med. & Biol. vol. 19, No. 2, pp. 123-125 (1993).

Smith, N. B., et al., "Non-lnvasive In Vivo Temperature Mapping of Ultrasound Heating Using Magnetic Resonance Techniques", 1994 Ultrasonics Symposium, pp. 1829-1832, vol. 3.

Surry et al., "Poly(vinyl alcohol) cryogel phantoms for use in ultrasound and MR imaging," Phys. Med. Biol., Dec. 6, 2004, pp. 5529-5546, vol. 49.

Syka J. E. P et al., "Peptide and Protein Sequence Analysis by Electron Transfer Dissociation Mass Spectometry," Proceedings of the National Academy of Sciences of USA, National Academy of Aceince, Washington, DC, vol. 101, No. 26, Jun. 29, 2004, pp. 9528-9533.

Talbert, D. G., "An Add-On Modification for Linear Array Real-Time Ultrasound Scanners to Produce 3D Displays," UTS Int'l 1977 Brighton, England (Jun. 28-30, 1977) pp. 57-67.

Tata et al., "Interaction of Ultrasound and Model Membrane Systems: Analyses and Predictions," American Chemical Society, Phys. Chem. 1992, 96, pp. 3548-3555.

Ueno, S., et al., "Ultrasound Thermometry in Hyperthermia", 1990 Ultrasonic Symposium, pp. 1645-1652.

Wang, H., et al., "Limits on Focused Ultrasound for Deep Hyperthermia", 1994 Ultrasonic Symposium, Nov. 1-4, 1994, pp. 1869-1872, vol. 3.

Wasson, S., "NVIDIA's GeForce 7800 GTX graphics processor Power MADD," http://techreport.com/reviews/2005q2/geforce-7800gtx/index.x?pg=1, Jun. 22, 2005, 4 pages.

White et al "Selective Creation of Thermal Injury Zones in the Superficial Musculoaponeurotic System Using Intense Ultrasound Therapy," Arch Facial Plastic Surgery, Jan./Feb. 2007, vol. 9, No. 1.

\* cited by examiner

METHODS AND SYSTEMS FOR ULTRASOUND ASSISTED DELIVERY OF A MEDICANT TO TISSUE

CROSS-REFERENCE TO RELATED APPLICATIONS

This application represents the national stage entry of PCT International Application PCT/US2016/020600 filed Mar. 3, 2016, which claims priority to, and incorporates herein by reference for all purposes U.S. patent application Ser. No. 14/637,237, filed Mar. 3, 2015, U.S. Provisional Patent Application No. 62/127,715 filed Mar. 3, 2015 and U.S. Provisional Patent Application 62/127,720 filed Mar. 3, 2015.

BACKGROUND

Trandermal delivery of medicants is limited primarily to the difficult-to-penetrate nature of the stratum corneum layer of skin. The stratum corneum layer forms a barrier that keeps moisture in and keeps practically everything else out. Accordingly, attempts to topically apply a medicant and deliver the medicant across the stratum corneum layer to tissue located beneath it must overcome this barrier property in order to be effect.

The bioavailability of topically applied medicants is typically very low. For example, the bioavailability of topically applied lidocaine is approximately 3%. See, Campbell, et al. J. Pharm. Sci. 91(5), pp. 1343-50 (May 2002). In other words, more than 30 times the desired amount of lidocaine needs to be applied topically for the desired effect. In the case of an expensive medicant or a medicant having various side effects, it is undesirable to require application of such an excess of medicant in order to have the desired effect.

Workarounds for this limited bioavailability of topically applied medicants generally include physically puncturing the skin, which is undesirable, because some patients can have aversion to the needles associated with such procedures.

Low-frequency sonophoresis is a known method for enhancing transdermal drug delivery. However, these existing methods employ low-frequencies, low peak intensities, require long application times, or some combination of these to achieve improved transdermal drug delivery.

Accordingly, a need exists for new systems and methods that overcome the aforementioned shortcomings.

SUMMARY

The present disclosure overcomes the aforementioned drawbacks by presenting systems and methods for ultrasound assisted delivery of a medicant to tissue.

In one aspect, this disclosure provides an ultrasound assisted medicant delivery system. The system can include an ultrasound probe and a control system. The ultrasound probe can include an ultrasound transducer. The ultrasound probe and the ultrasound transducer can be configured for coupling to a medicant administered to a skin surface. The control system can be electronically coupled to the ultrasound trasndcuer. The control system can, in use, cause the ultrasound transducer to apply a first pulse acoustic energy field to the skin surface. The first pulsed acoustic energy field can have a frequency from 1 MHz to 30 MHz, a peak intensity from 100 W/cm$^2$ to 100 kW/cm$^2$, and a pulse width from 33 nanoseconds to 5 seconds. The first pulsed acoustic energy field can generate inertial cavitation, acoustic streaming, or a combination thereof in the stratum corneum layer and drive the medicant through the stratum corneum layer.

In another aspect, this disclosure provides a method for ultrasound assisted delivery of a medicant through a stratum corneum layer of a skin surface. The method can include: administering the medicant to a skin surface; coupling an ultrasound transducer to the medicant and the skin surface; and applying a first pulse acoustic energy field from the ultrasound transducer to the skin surface. The first pulse acoustic energy field can have a frequency from 1 MHz to 30 MHz, a peak intensity from 100 W/cm$^2$ to 100 kW/cm$^2$, and a pulse width from 33 nanoseconds to 5 seconds. The first pulsed acoustic energy field can generate inertial cavitation, acoustic streaming, or a combination thereof in the stratum corneum layer and drive the medicant through the stratum corneum layer.

In a further aspect, this disclosure provides a method for reducing or eliminating pain generated by ultrasound treatment. The method can include: applying a coupling medium comprising a medicant to a skin surface above a region of intere, the medicant comprising an anesthetic configured to numb a tissue in the region of interest; coupling an ultrasound energy source to the coupling medium, the skin surface, and the region of interest; directing a first acoustic energy field from the ultrasound energy source into the skin surface, thereby delivering the medicant into the tissue in the region of interest and numbing the tissue in a portion of the region of interest; and directing a second acoustic energy field to a target volume in the tissue in the region of interest, the second acoustic energy field ablating the tissue in the target volume, the medicant reducing or eliminating pain generated by the ablating of the tissue.

In yet another aspect, this disclosure provides a method of ultrasound assisted transdermal drug delivery. The method can include: contacting a skin surface with a coupling medium comprising a non-anesthetic medicant and an anesthetic; coupling an ultrasound energy source to the coupling medium and the skin surface; and applying a first pulsed acoustic energy field from the ultrasound transducer to the skin surface. The first pulse acoustic energy field can have a peak intensity from 100 W/cm$^2$ to 100 kW/cm$^2$. The first pulsed acoustic energy field can drive the medicant and the anesthetic across a stratum corneum layer of the skin surface and into an epidermis layer beneath the skin surface. The anesthetic can alleviate pain or swelling associated with the application of the first pulsed acoustic energy field.

The foregoing and other aspects and advantages of the invention will appear from the following description. In the description, reference is made to the accompanying drawings which form a part hereof, and in which there is shown by way of illustration a preferred aspect of the disclosure. Such aspect does not necessarily represent the full scope of the disclosure, however, and reference is made therefore to the claims and herein for interpreting the scope of the disclosure.

DETAILED DESCRIPTION

Figure 1A:
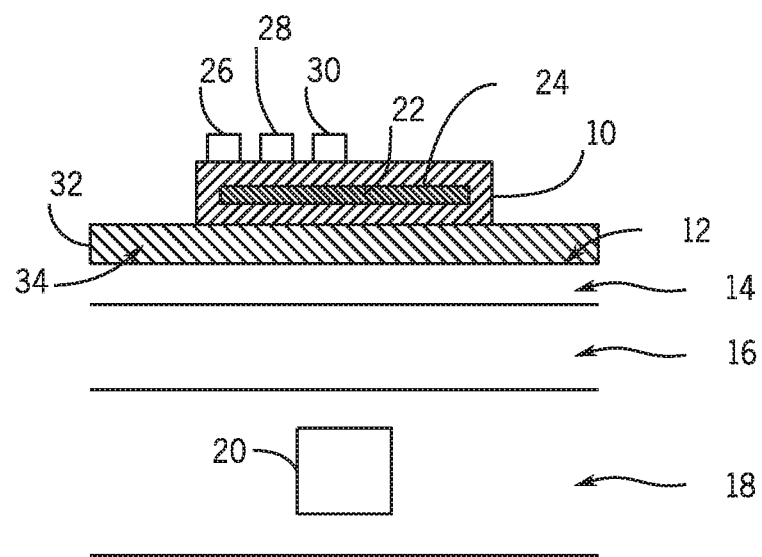
FIG. 1A illustrates an ultrasound assisted drug delivery probe and a first stage of a method of its use, according to one aspect of the present disclosure.

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

Specific structures, devices, and methods relating to improved ultrasound treatment efficiency and operation are disclosed. It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements.

This disclosure provides methods and systems for enhancing medicant delivery across the stratum corneum layer of skin and into the epidermis layer. The systems and methods also facilitate movement of the medicant deeper into the epidermis or into the dermis layer and subcutaneous tissue beneath the dermis layer.

As will be described with respect to FIGS. 1A, 1B, 1C, and 1D, an ultrasound assisted drug delivery probe 10 can be positioned atop and coupled to a skin surface 12. The skin surface 12 can be located above a stratum corneum 14, an epidermis 16, and a dermis 18. A region of interest 20 can be any contiguous location within the illustrated skin surface 12, the stratum corneum 14, the epidermis 16, the dermis 18, or a combination thereof. The region of interest 20 can be a region of interest as described herein. The ultrasound assisted drug delivery probe 10 can include an ultrasound source 22, which can include one or more transducers 24. The ultrasound source 22 can be any source described herein. The transducers 24 can be any transducers described herein. The one or more transducers 24 can each independently be a single transduction element, an array of transduction elements, or a group of arrays of transduction elements. The ultrasound assisted drug delivery probe 10 can be coupled to a power supply 26 and electronics 28 sufficient for the operation of an ultrasound system. The power supply 26 can be any power supply known to one of skill in the art to be suitable for powering an ultrasound probe, such as any power supply described herein, among others. The electronics 28 can be any electronics known to one of skill in the art to be suitable for operating an ultrasound probe, such as any electronics described herein, among others. The ultrasound assisted drug delivery probe 10 can be coupled to a control module 30 adapted to control the emission of ultrasound from the ultrasound assisted drug delivery probe 10. The control module 30 can be any control module or controller known to one of skill in the art to be suitable for controlling the emission characteristics of an ultrasound probe, such as any control module or controller described herein, among others.

Examples of suitable power supplies 26 can include, but are not limited to, one or more direct current (DC) power supplies, single-use or rechargeable batteries, or other power supplies configured to provide electrical energy to the ultrasound assisted drug delivery probe 10, including to the ultrasound source 28, transducers 30, electronics 28, control modules 30, or any other aspect of the ultrasound assisted drug delivery probe 10 that requires electrical energy. Associated sensors for monitoring the performance of the power supplies 26 are contemplated, such as current sensors, power sensors, and the like.

Examples of suitable electronics 28 can include, but are not limited to, amplifiers or drivers, such as multi-channel or single channel power amplifiers or drivers; power converters configured to adjust voltages; open-loop feedback systems; closed-loop feedback systems; filters, such as harmonic filters or matching filters; and the like.

Control modules 30 can include components suitable for controlling the emission characteristics of the ultrasound assisted drug delivery probe 10, including but not limited to, a computing system adapted to control the ultrasound assisted drug delivery probe 10; timing circuits; software and algorithms to provide control and user interfacing; input controls, such as switches, buttons, touchscreens, and the like; outputs, such as lighting or audio signals or displays; storage elements, such as memory to store calibration and usage data; and the like.

The ultrasound assisted drug delivery probe 10 can also include sensors suitable for measuring certain aspects of the ultrasound assisted drug delivery probe 10. Examples of sensors include, but are not limited to, temperature sensors, motion sensors, location sensors, coupling sensors, such as capacitive or acoustic coupling sensors, and the like.

The transducer 30 can be configured as a spherically-focused single element transducer, an annular/multi-element transducer, an annular array having an imaging region, a line-focused single-element transducer, a one-dimensional linear array, a one-dimensional curved linear array, a two-dimensional array with a mechanical focus, a convex lens focus, a concave lens focus, a compound lens focus, or a multiple lens focus, a two-dimensional planar array, or other transducer arrangements suitable for producing the ultrasound energy described herein and corresponding effects.

Referring to FIG. 1A, the ultrasound assisted drug delivery probe 10 can be coupled to the skin surface 12 by way of a coupling medium 32. The coupling medium 32 can include a medicant 34.

Figure 1B:
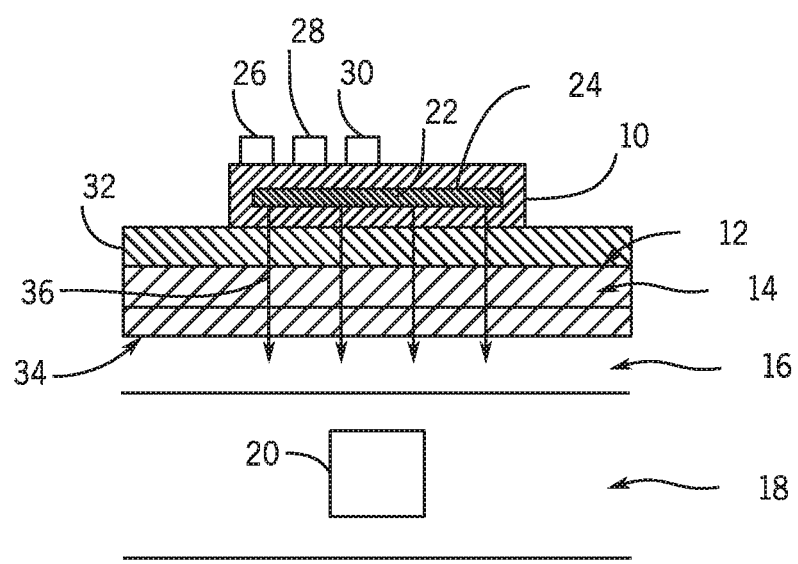
FIG. 1B illustrates an ultrasound assisted drug delivery probe and a second stage of a method of its use, according to one aspect of the present disclosure.

Referring to FIG. 1B, the arrangement illustrated in FIG. 1A is illustrated after the ultrasound assisted drug delivery probe 10 has begun emitting a first acoustic energy field 36 that penetrates at least through the skin surface 12 and the stratum corneum 14 and penetrates at least partially into the epidermis 16. In response to the first acoustic energy field 36, the medicant 34 can be driven from above the skin surface 12 through the skin surface 12, into or through the stratum corneum 14, and into the epidermis 16.

It should be appreciated that there exist intermediate states between the state of the arrangement illustrated in FIG. 1A and that illustrated in FIG. 1B, where the first acoustic energy field 36 penetrates only partially into the stratum corneum 14, or penetrates throughout the stratum corneum 14 but not into the epidermis 16, or penetrates throughout the stratum corneum 14 and partially into the epidermis 16 to a depth different than that illustrated. In similar intermediate states, the medicant 34 can penetrate only partially into the stratum corneum 14, or penetrates throughout the stratum corneum 14 but not into the epidermis 16, or penetrates throughout the stratum corneum 14 and partially into the epidermis 16 to a depth different than that illustrated.

Figure 1C:
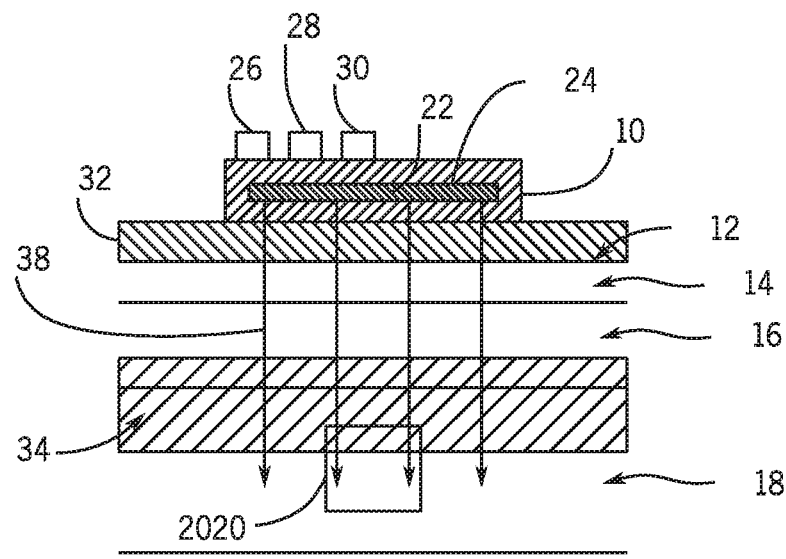
FIG. 1C illustrates an ultrasound assisted drug delivery probe and a third stage of a method of its use, according to one aspect of the present disclosure.

Referring to FIG. 1C, the arrangement illustrated in FIGS. 1A and 1B is illustrated after the ultrasound assisted drug delivery probe 10 has begun emitting a second acoustic energy field 38 that penetrates at least through the skin surface 12, the stratum corneum 14, and the epidermis 16, and penetrates at least partially into the dermis 18. In response to the second acoustic energy field 38, the medicant 34 can be driven from the epidermis 16 to a deeper portion of the epidermis 16 or into the dermis 18.

It should be appreciated that there exist intermediate states between the state of the arrangement in FIG. 1B and that illustrated in FIG. 1C, where the second acoustic energy field 38 can penetrate throughout the epidermis 16 but not into the dermis 18, or can penetrate through the epidermis 16 and partially into the dermis 18, or can penetrate into the dermis 18 to a depth different than that illustrated. In similar intermediate states, the medicant 34 can penetrate throughout the epidermis 16 but not into the dermis 18, or can penetrate through the epidermis 16 and partially into the dermis 18, or can penetrate into the dermis 18 to a depth different than that illustrated.

Figure 1D:
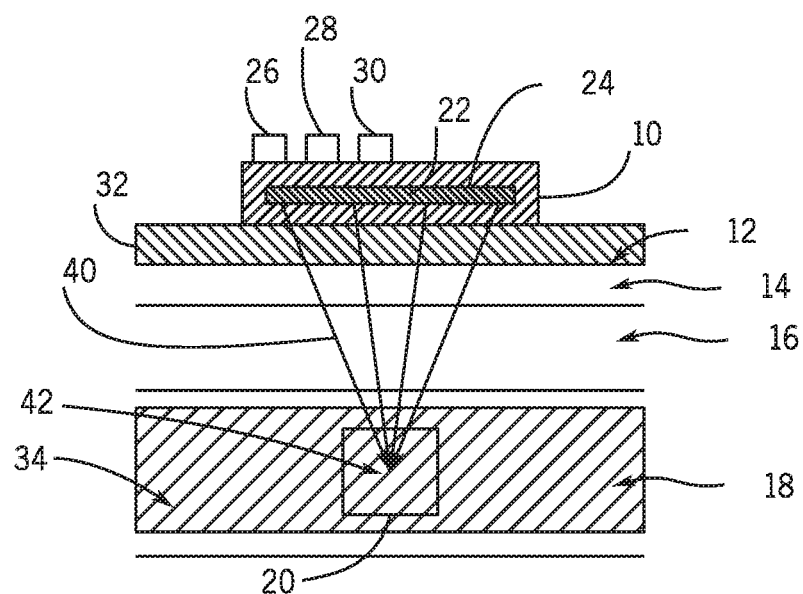
FIG. 1D illustrates an ultrasound assisted drug delivery probe and a fourth stage of a method of its use, according to one aspect of the present disclosure.

Referring to FIG. 1D, the arrangement illustrated in FIGS. 1A, 1B, and 1C is illustrated after the medicant 34 has been driven into the dermis 18. In the dermis 18, the medicant 34 can interact with tissue or enter the blood stream via capillaries. In certain applications, a third acoustic energy field 40, optionally referred to as a therapeutic acoustic energy field 40, can be directed to a target volume 42 within the dermis 18. The target volume 42 can be located in a portion of the dermis 18 containing the medicant 34.

A method for ultrasound-assisted delivery of a medicant through a stratum corneum layer of a skin surface can include the following steps: administering the medicant to the skin surface; coupling an ultrasound transducer to the medicant and the skin surface; and applying a first pulsed acoustic energy field from the ultrasound transducer to the skin surface, the first pulsed acoustic energy field having one or more of the properties described elsewhere herein, the first pulsed acoustic energy field generating intertial cavitation, acoustic streaming, or a combination thereof in the stratum corneum layer and driving the medicant through the stratum corneum layer.

As will be described with respect to FIGS. 2A, 2B, 2C, and 2D, a delivery system 44 can include an ultrasound assisted drug delivery probe 10 and a standoff 46 comprising a medicant 34. The ultrasound assisted drug delivery probe 10 can include features described elsewhere herein. The standoff 46 can include a plurality of pores in a bottom surface 48, the plurality of pores being in fluid communication with the medicant 34. The plurality of pores can be of a size and shape that are sufficient to retain the medicant 34 within the standoff 46. In certain aspects, the medicant 34 is retained in the standoff 46 by virtue of a surface tension of the medicant 34. In certain aspects, the standoff 46 can include a gel pack coupled to the ultrasound assisted drug delivery probe 10. In certain aspects, the standoff 46 can be rigid or flexible.

Figure 2A:
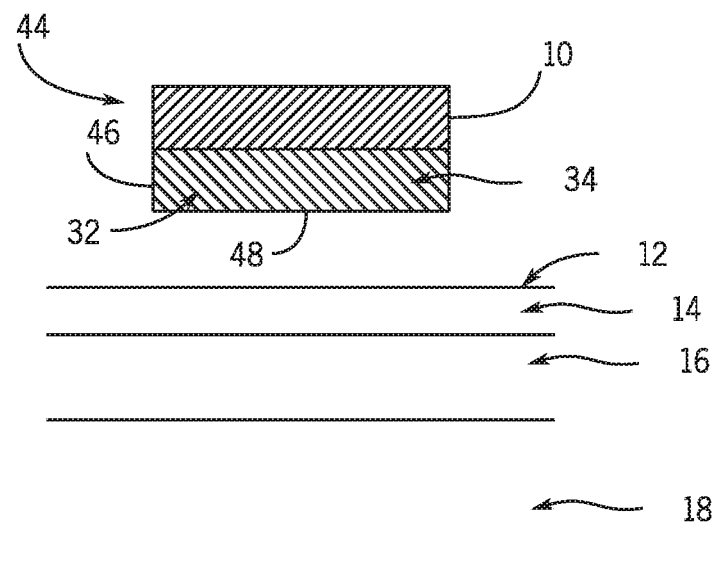
FIG. 2A illustrates an ultrasound assisted drug delivery probe and a first stage of a method of its use, according to one aspect of the present disclosure.
Figure 2B:
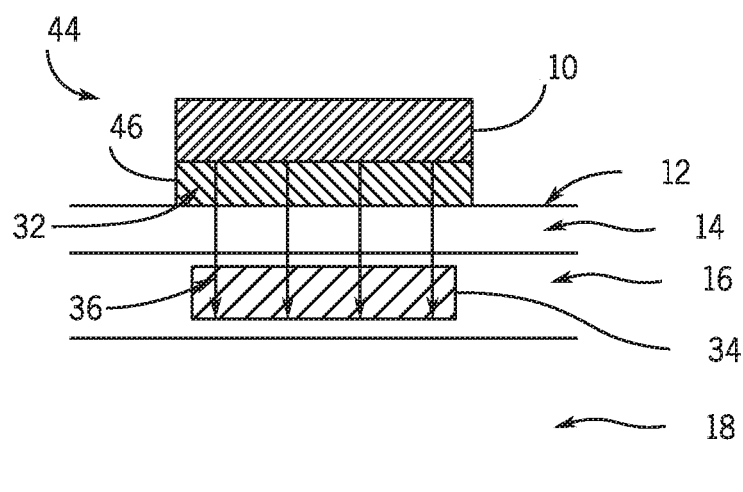
FIG. 2B illustrates an ultrasound assisted drug delivery probe and a second stage of a method of its use, according to one aspect of the present disclosure.

Referring to FIG. 2A, the delivery system 44 is positioned above the skin surface 12. In FIG. 2B, the arrangement illustrated in FIG. 2A is illustrated after the delivery system 44 has been coupled to the skin surface 12. The ultrasound assisted drug delivery probe 10 can emit a first acoustic energy field 36 that penetrates at least through the skin surface 12 and the stratum corneum 14 and penetrates at least partially into the epidermis 16. In response to the first acoustic energy field 36, the medicant 34 can be driven from above the skin surface 12 through the skin surface 12, into or through the stratum corneum 14, and into the epidermis.

It should be appreciated that there exist intermediate states between the state of the arrangement in FIG. 2A and that illustrated in FIG. 2B, where the first acoustic energy field 36 can penetrate only partially into the stratum corneum 14 or can penetrate throughout the stratum corneum 14 but not into the epidermis 16, or can penetrate through the stratum corneum 14 and partially into the epidermis 16 to a depth different than that illustrated. In similar intermediate states, the medicant 34 can penetrate only partially into the stratum corneum 14, or can penetrate throughout the stratum corneum 14 but not into the epidermis 16, or can penetrate throughout the stratum corneum 14 and partially into the epidermis 16 to a depth different than that illustrated.

Figure 2C:
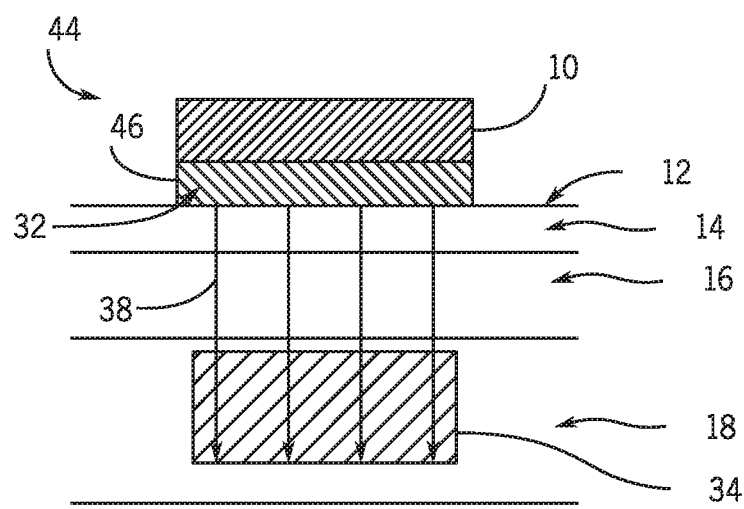
FIG. 2C illustrates an ultrasound assisted drug delivery probe and a third stage of a method of its use, according to one aspect of the present disclosure.

Referring to FIG. 2C, the arrangement illustrated in FIGS. 2A and 2B is illustrated after the ultrasound assisted drug delivery probe 10 has begun emitting a second acoustic energy field 38 that penetrates at least through the skin surface 12, the stratum corneum 14, and the epidermis 16, and penetrates at least partially into the dermis 18. In response to the second acoustic energy field 38, the medicant 34 can be driven from the epidermis to a deeper portion of the epidermis 16, partially into the dermis 18, or entirely into the epidermis.

It should be appreciated that there exist intermediate states between the state of the arrangement in FIG. 2B and that illustrated in FIG. 2C, where the second acoustic energy field 38 can penetrate throughout the epidermis 16 but not into the dermis 18, or can penetrate through the epidermis 16 and partially into the dermis 18, or can penetrate into the dermis 18 to a depth different than that illustrated. In similar intermediate states, the medicant 34 can penetrate throughout the epidermis 16 but not into the dermis 18, or can penetrate through the epidermis 16 and partially into the dermis 18, or can penetrate into the dermis 18 to a depth different than that illustrated.

Figure 2D:
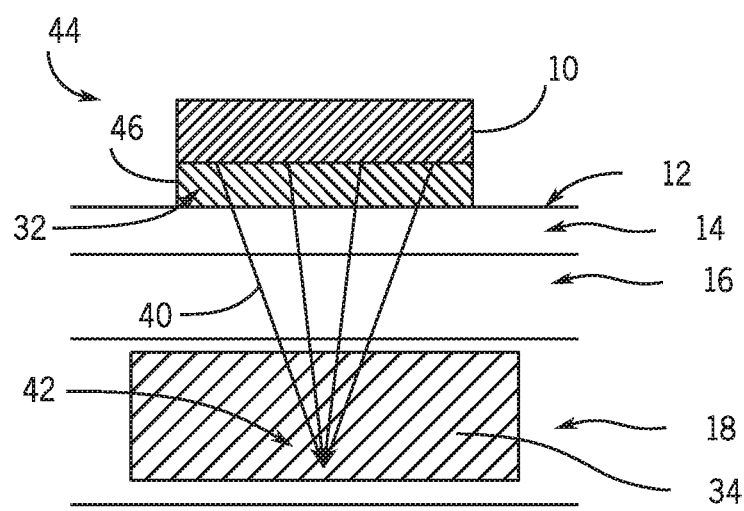
FIG. 2D illustrates an ultrasound assisted drug delivery probe and a fourth stage of a method of its use, according to one aspect of the present disclosure.

Referring to FIG. 2D, the arrangement illustrated in FIGS. 2A, 2B, and 2C is illustrated after the medicant 34 has been driven into the dermis 18. In the dermis, the medicant 34 can interact with the tissue or enter the blood stream via capillaries. In certain applications, a third acoustic energy field 40, optionally referred to as a therapeutic acoustic energy field 40, can be directed to a target volume 42 within the dermis 18. The target volume 42 can be located in a portion of the dermis 18 containing the medicant 34.

In certain aspects, the delivery system 44 can be configured as a transdermal patch. For example, the delivery system 44 can be configured for off-the-shelf operation, where the delivery system 44 include the medicant 34 in appropriate dosage within the standoff 46 and a suitable portable power supply, such as battery power, to power the delivery system 44. After removing any packaging for the delivery system 44, the delivery system 44 can be applied to a location by a patient or a user. In certain aspects, the delivery system 44 can include an adhesive material on the bottom surface 48 of the standoff 46 or a patch that extends over the ultrasound assisted drug delivery probe 10 to facilitate retention of coupling between the probe 10 and the skin surface 12.

In certain aspects, the delivery system 44 can have an on-off switch or a separate on-off device that allows a patient or user to turn the delivery system 44 on (and subsequently off) when the ultrasound assisted drug delivery probe 10 is properly located on the skin surface 12. The delivery system 44 can utilize at least one ultrasound energy effect to move the medicant 34 from the standoff 46 to below the skin surface 12.

A delivery system 44 as described herein can have significant advantages over a traditional transdermal patch. For example, the delivery system 44 can deliver medicants 34 having a higher molecular weight, for example, medicants 34 having a molecular weight of at least about 100 Da or at least about 500 Da. As another example, the delivery system 44 does not rely on mechanical diffusion, so lower doses of the medicant 34 can be deployed because more of the medicant 34 reaches areas beneath the skin surface 12. As yet another example, the delivery system 44 is not limited to deploying medicants 34 having an affinity for both lipophilic and hydrophilic phases or medicants 34 that are non-ionic. In certain aspects, the delivery system 44 can include a solar panel, which can optionally be no bigger than the area of a patch covering the ultrasound assisted drug delivery probe 10, to supplement power to the delivery system 44.

Figure 3:
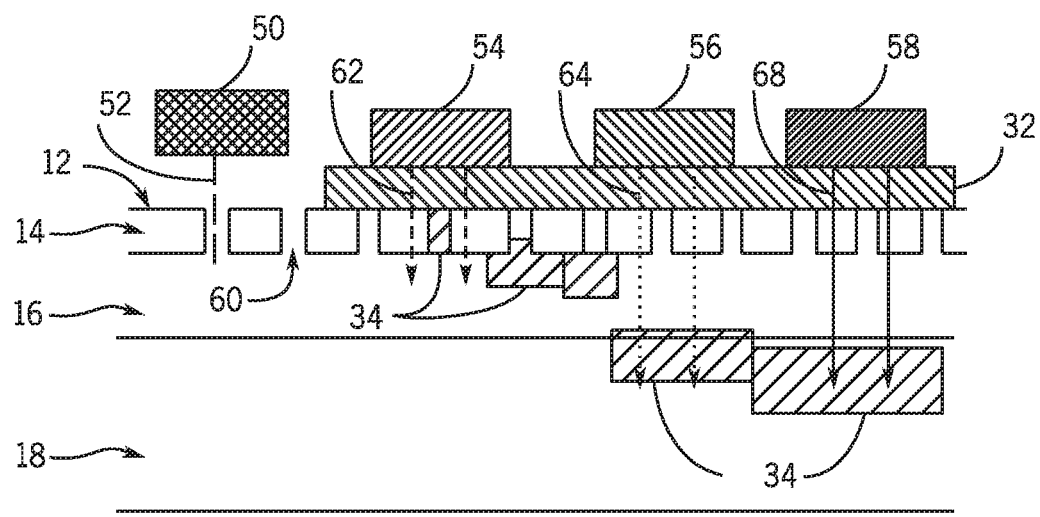
FIG. 3 illustrates a set of components for use in an ultrasound assisted drug delivery system, according to one aspect of the present disclosure.

Referring to FIG. 3, multiple devices, including a microchannel device 50 comprising a microchannel creation means 52, a first ultrasound device 54, a second ultrasound device 56, and a third ultrasound device 58, can be configured individually or as a part of a single system to independently or cooperatively provide delivery of a medicant 34. The microchannel device 50 comprising the microchannel creation means 52 is configured to create a microchannel 60 through the stratum corneum 14. The microchannel device 50 and microchannel creation means 52 can be any of the systems or methods described herein. For example, the microchannel device 50 can be an ultrasound probe and the microchannel creation means 52 can employ one or more acoustic energy fields, such as described in the description of FIGS. 1A, 1B, 1C, 1D, 2A, 2B, 2C, and 2D. The microchannel device 50 microchannel creation means 52 can also include one or more microneedles. The microchannel device 50 can be a photon-based energy source and the microchannel creation means 52 can include a photon-based energy field configured to generate microchannels 60 in the stratum corneum 14.

The microchannel device 50, the first ultrasound device 54, the second ultrasound device 56, and the third ultrasound device 58 can move from right to left across the illustrated skin surface 12, either collectively or independently. A coupling medium 32 can be applied to the skin surface 12 before or after the microchannel creation means 52 has created a microchannel 60. If the microchannel device 50, the first ultrasound device 54, the second ultrasound device 56, and the third ultrasound device 58 are operating in series, then the coupling medium 32 is typically applied to the skin surface 12 after the microchannel creation means 52 has created the microchannel 60 to avoid loss of the medicant 34 or contamination of the medicant 34 by the microchannel creation means 52. The microchannel device 50, the first ultrasound device 54, the second ultrasound device 56, and the third ultrasound device 58 can be controlled by a control module 30, either collectively or independently. In certain aspects, the microchannel device 50, the first ultrasound device 54, the second ultrasound device 56, and the third ultrasound device 58 can each be housed in individual cylinders or spheres that are configured to roll across the skin surface 12.

The first ultrasound device 54 can be configured to direct a fourth acoustic energy field 62 into the skin surface 12. The fourth acoustic energy field 62 can be configured to drive the medicant 34 through the microchannel 60. In certain aspect, the fourth acoustic energy field 62 can have the properties of the first acoustic energy field 36, as described herein.

The second ultrasound device 56 can be configured to direct a fifth acoustic energy field 64 into the skin surface 12. The fifth acoustic energy field 64 can be configured to drive the medicant 34 through the epidermis 16 and optionally through the dermis 18. In certain aspects, the fifth acoustic energy field 64 can have the properties of the second acoustic energy field 38, as described herein.

The third ultrasound device 58 can be configured to direct a sixth acoustic energy field 66 into the skin surface 12. The sixth acoustic energy field 66 can be configured to interact with the medicant 34 or with tissue containing or proximate to the medicant 34. In certain aspect, the sixth ultrasound acoustic energy field 66 can have the properties of the third acoustic energy field 40, as described herein.

In addition to the first acoustic energy field 36, the second acoustic energy field 38, the third acoustic energy field 40, the fourth acoustic energy field 62, the fifth acoustic energy field 64, or the sixth acoustic energy field 66, the methods described herein can utilize additional acoustic energy fields configured to provide one or more effects described herein.

In certain aspects, a system such as an ultrasound assisted drug delivery probe 10, a delivery device 44, a microchannel device 50, a first ultrasound device 40, a second ultrasound device 56, a third ultrasound device 58, or any combination thereof can include various components described herein. For example, a system can include a control module 30. As one non-limiting example, such a control module 30 can be the control module 20 described above, which can be configured to receive at least one communication and control a distribution of the acoustic energy field transmitted by the ultrasound energy source, such as, for example, an acoustic transducer 24. The control module 30 can be configured to receive a treatment start signal and a treatment stop signal. The control module 30 can be programmed to provide treatment to the ROI 20 for a desired outcome. The control module 30 can initiate and run a treatment program (treatment function), which can include the control of spatial parameters and/or temporal parameters of the ultrasound source, to provide programmed distribution of the acoustic energy field in the ROI 20. The control module 30 can be configured to receive feedback from one or more sensors and/or detectors, and the control module 30 can terminate the treatment program based on the feedback.

The control module 30 can be configured to communicate with the probe 10 via wireless interface. In some embodiments, the control module 20 can be a wireless device, which has a display and a user interface such as, for example, a keyboard. Examples of a wireless device can include but are not limited to: a personal data assistant (PDA), a cell phone, a smart phone, an iPhone, an iPad, a computer, a laptop, a netbook, a tablet, or any other such device now known or developed in the future. Examples of wireless interface include but are not limited to any wireless interface described herein and any such wireless interface now known or developed in the future. Accordingly, the probe 10 can comprise any hardware, such as, for example, electronics, antenna, and the like, as well as, any software that may be used to communicate via wireless interface.

The wireless device can be configured to display an image generated by the probe 10. The wireless device can be configured to control at least a portion of the probe 10. The wireless device can be configured to store data generated by the probe 10 and sent to the wireless device.

Various sensing and monitoring components may also be implemented within control module. For example, monitoring, sensing, and interface control components may be capable of operating with the motion detection system implemented within the probe 10, to receive and process information such as acoustic or other spatial and temporal information from the ROI 20. Sensing and monitoring components may also comprise various controls, interfacing, and switches and/or power detectors. Such sensing and monitoring components may facilitate open-loop and/or closed-loop feedback systems within the probe 10.

In some aspects, sensing and monitoring components may further comprise a sensor that may be connected to an audio or visual alarm system to prevent overuse of the probe 10. The sensor may be capable of sensing the amount of energy transferred to the skin, and/or the time that the probe 10 has been actively emitting the acoustic energy. When a certain time or temperature threshold has been reached, the alarm may sound an audible alarm, or cause a visual indicator to activate to alert the user that a threshold has been reached. This may prevent overuse of the device. In some embodiments, the sensor may be operatively connected to the control module and force the control module 30, to stop emitting the acoustic energy from the probe 10. In some embodiments, the control module 30 is operable to control the power supply to change an amount of power provided to the acoustic transducer 24 in the probe 10.

A position sensor may be located behind a transducer, in front of a transducer, or integrated into a transducer array. The probe 18 may comprise more than one position sensor, such as, for example, a laser position sensor and a motion sensor, or a laser position sensor and a visual device, or a motion sensor and a visual device, or a laser position sensor, a motion sensor, and a visual device. In some embodiments, position sensor may determine a distance between pulses of the acoustic energy to create a plurality of treatment zones which are evenly spaced or disposed in any spatial configuration in 1-D or 2-D patterns. As the probe 18 is moved in direction, the position sensor determines distance, regardless of a speed that the ultrasound source is move, at which a pulse of acoustic energy is to be emitted in to ROI 12.

In some aspects, the system can further comprise a contact sensor operable to determine if the ultrasound source is coupled to the ROI 12. The tissue contact sensor can communicate to the control module 20 whether the ultrasound source is coupled to the ROI 12.

The first acoustic energy field 36, second acoustic energy field 38, or third acoustic energy field 40 can be planar, focused, weakly focused, unfocused, or defocused. The first acoustic energy field 36, second acoustic energy field 38, or third acoustic energy field 40 can have a frequency in the range of about 1 MHz to about 30 MHz, including, but not limited to, a frequency in the range of about 5 MHz to about 15 MHz, from about 2 MHz to about 12 MHz, from about 3 MHz to about 7 MHz, from about 1 MHz to about 7 MHz, from about 2 MHz to about 5 MHz, from about 3 MHz to about 10 MHz, or from about 1 MHz to about 10 MHz, or other combinations of the lower and upper limits of these ranges not explicitly recited. The first acoustic energy field 36, second acoustic energy field 38, or third acoustic energy field 40 can be configured to avoid damaging the cells in the stratum corneum 14 or the epidermis 16.

The first acoustic energy field 36, second acoustic energy field 38, or third acoustic energy field 40 can be pulsed and have a delay of from about 1 µs to about 100 seconds between pulses. The first acoustic energy field 36, second acoustic energy field 38, or third acoustic energy field 40 can be continuous wave. In certain aspects, the first acoustic energy field 36, second acoustic energy field 38, or third acoustic energy field 40 can be pulsed and have a pulse repetition rate of one pulse per 10 µs to one pulse per 100 seconds.

In certain applications, such as generating inertial cavitation in the stratum corneum 14 which can create microchannels having an intercellular route from the skin surface 12 to the epidermis 16, the first acoustic energy field 36 can have a pulse width in a range from about 33 ns to about 100 s. In these certain applications, the first acoustic energy field 36 can be pulsed and can have a pulse width in the range of about 1 µs to about 1 second, or in the range of about 0.01 seconds to about 5 seconds. In these certain applications, the first acoustic energy field 36 can have a peak intensity of greater than 3 W/cm$^2$ and less than or equal to about 100 kW/cm$^2$ at the skin surface 12. In certain aspects, the first acoustic energy field 36 can have a peak intensity of greater than 10 W/cm$^2$, greater than 50 W/cm$^2$, greater than 100 W/cm$^2$, greater than 300 W/cm$^2$, greater than 500 W/cm$^2$, greater than 1 kW/cm$^2$, greater than 3 kW/cm$^2$, or greater than 5 kW/cm$^2$. The intensity of the first acoustic energy field 36 can be below a threshold value for creating a shock wave. A person having ordinary skill in the art will appreciate that this threshold value can vary based on material properties and the specific parameters of the ultrasound being used, and can determine this threshold value for specific materials and sets of parameters experimentally or computationally.

In certain applications, such as generating acoustic streaming providing acoustic streaming pressure to the stratum corneum 14, the epidermis 16, or a combination thereof, the first acoustic energy field 36 can be pulsed and the pulses can have a pulse width in a range of about 33 ns to about 100 s, including, but not limited to, a range of about 1 µs to about 10 seconds or a range of about 0.001 seconds to about 5 seconds. In these certain applications, the first acoustic energy field 36 can have a peak intensity in the range from about 5 W/cm$^2$ to about 100 kW/cm$^2$ at the skin surface 12.

In certain aspects, the first acoustic energy field 36 can have a peak intensity of greater than 10 W/cm$^2$, greater than 50 W/cm$^2$, greater than 100 W/cm$^2$, greater than 300 W/cm$^2$, greater than 500 W/cm$^2$, greater than 1 kW/cm$^2$, greater than 3 kW/cm$^2$, or greater than 5 kW/cm$^2$. Acoustic streaming can generate microchannels having a transcellular route from the skin surface 12 to the epidermis 16. In these certain applications, acoustic streaming generated by the first acoustic energy field 36 can create pressures ranging from about 10 kPa to about 120 MPa, including, but not limited to, pressures ranging from about 10 kPa to about 10 MPa and pressures ranging from about 10 MPa to about 120 MPa, in the stratum corneum 14, the epidermis 16, or a combination thereof.

In certain applications, such as generating inertial cavitation in the stratum corneum 14 and acoustic streaming providing acoustic streaming pressure to the stratum corneum 14, the epidermis 16, or a combination thereof, which can generate microchannels having both an intercellular route and a transcellular route from the skin surface 12 to the epidermis 16, the first acoustic energy 36 can provide two or more effects, such as inertial cavitation and acoustic streaming, simultaneously or alternating. In certain aspects, generating inertial cavitation and acoustic streaming can facilitate moving a larger medicant, such as a medicant with a molecular weight greater than 500 Da, through the stratum corneum 14.

In certain applications, the second acoustic energy 38 can be configured to generate inertial cavitation or acoustic streaming in the epidermis 16, the dermis 18, or a combination thereof. In certain aspects, the second acoustic energy 38 can be configured to increase diffusion of the medicant 34 through the epidermis 16 and the dermis 18. In certain aspects, the second acoustic energy 38 can provide a pressure in a range from about 100 kPa to about 100 MPa to push the medicant 34 through the epidermis 16 and into the dermis 18.

It should be appreciated that the effects described herein are tissue-dependent, so the ultrasound energy necessary to generate inertial cavitation or acoustic streaming in one type of tissue might be different than the ultrasound energy necessary to generate inertial cavitation or acoustic streaming in a different type of tissue. It should also be appreciated that for a certain effect to be generated, the threshold for generating that effect must be exceeded. However, the thresholds for generating the effects described herein, such as inertial cavitation and subsequent acoustic streaming, in tissues are generally unknown.

With respect to inertial cavitation, aside from a single experimental study regarding the frequency-dependence of the threshold for inertial cavitation in canine skeletal muscle, a recent article by Church et al. states that "too little information on the experimental threshold for inertial cavitation in other tissues is available" to make conclusions regarding frequency-dependent trends. See, Church C C, et al. "Inertial cavitation from ARFI imaging and the MI", Ultrasound in Med. & Biol., Vol. 41, No. 2, pp. 472-485 (2015). This observation is solely about the inertial cavitation threshold as it relates to frequency, and does not take into account the other spatial and temporal parameters aside from frequency. Accordingly, one of skill in the art should appreciate that the present invention is disclosed in terms of effects that have been shown to produce a specific result, i.e., transporting a medicant across the stratum corneum, and a set of general parameters that are suitable for achieving that result are set forth above. One of skill in the art should also appreciate that the presence of inertial cavitation can be identified by a characteristic broadband signal that is the result of the complex dynamics associated with inertial cavitation.

With respect to acoustic streaming, this effect can be generated by an effect including the aforementioned inertial cavitation or without the inertial cavitation. In instances without the inertial cavitation, acoustic streaming can be accomplished by introducing heat into a tissue, for example the stratum corneum, which expands the tissue, then applying a pressure to the medicant or a carrier containing the medicant to initiate acoustic streaming.

The inertial cavitation and acoustic streaming effects are described herein with respect to the discrete layers of the skin, but can penetrate to a greater depth beneath the skin surface to enhance the penetration of the medicant deeper into the skin or into subcutaneous tissue.

In certain aspects, the first acoustic energy 36 and the second acoustic energy 38 can be substantially the same. In certain aspects, the second acoustic energy 38 can have a frequency that concentrates the acoustic energy deeper and moves the medicant 34 into the dermis 18. In certain aspects, the second acoustic energy 38 can be configured to cause a thermal effect in the epidermis 16 or the dermis 18, which is non-destructive to the cells of the epidermis 16 or dermis 18.

The first acoustic energy 36, second acoustic energy 38, or third acoustic energy 40 can be generated from one or more ultrasound sources.

In certain aspects, the ultrasound assisted drug delivery probe 10 can be configured to create an intensity gain from the ultrasound assisted drug delivery probe 10 to the target volume 42 of at least about 5, including, but not limited to, an intensity gain of at least about 10, at least about 25, at least about 50, or at least about 100. In aspects having a focused or a strongly focused ultrasound, the ultrasound assisted drug delivery probe 10 can be configured to create an intensity gain from the ultrasound assisted drug delivery probe 10 to the target volume 42 of at least about 50, including, but not limited to, an intensity gain of at least about 100, or at least about 500. In aspects having a weakly focused ultrasound, the ultrasound assisted drug delivery probe 10 can be configured to create an intensity gain from the ultrasound assisted drug delivery probe 10 to the target volume 42 of at least about 5.

In certain aspects with pulsed ultrasound, a first pulse can be ultrasound having a first type of focus, a second pulse can be ultrasound having a second type of focus, a third pulse can be ultrasound having the first type of focus or a third type of focus, and so on. Any combination of focused, defocused, or unfocused energy can be used for any of the various pulses.

In certain aspects, the first acoustic energy 36, second acoustic energy 38, or third acoustic energy 40 can create a thermal effect, a mechanical effect, or a combination thereof in the target volume 42. A mechanical effect is a non-thermal effect within a medium that is created by acoustic energy. A mechanical effect can be one of, for example, acoustic resonance, acoustic streaming, disruptive acoustic pressure, shock waves, inertial cavitation, and non-inertial cavitation.

Figure 4:
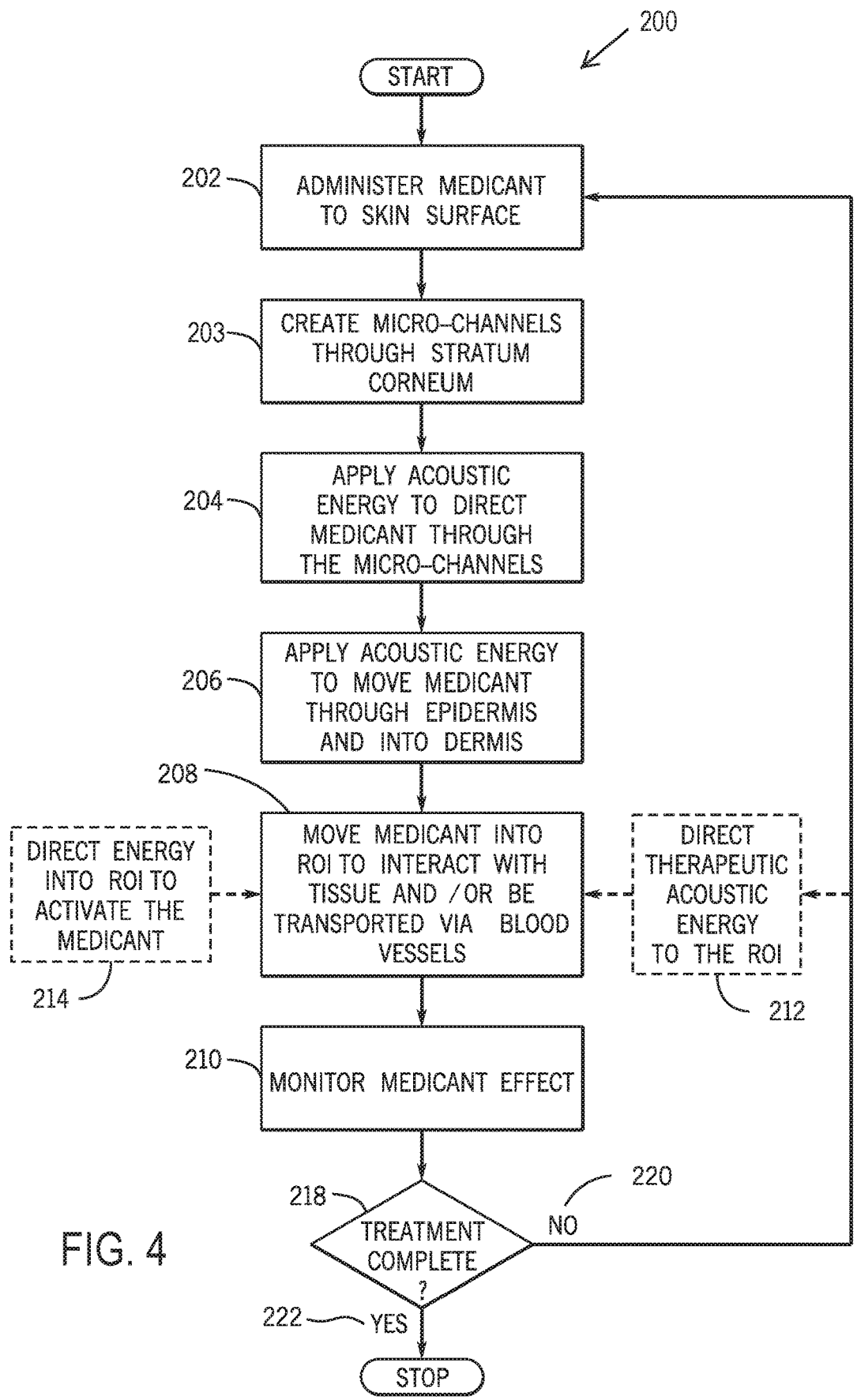
FIG. 4 is a flowchart illustrating methods of ultrasound assisted drug delivery, according to one aspect of the present disclosure.

Referring to FIG. 4, a flowchart illustrating a method 200 of ultrasound assisted drug delivery is provided. At process block 202, the method 200 can include administering a medicant 34 to a skin surface 12. At process block 203, the method 200 can include creating microchannels 60 through the stratum corneum 14. At process block 204, the method 200 can include applying a first acoustic energy field 36 to direct the medicant 34 through the microchannels 60. At process block 206, the method 200 can include applying a second acoustic energy field 38 to direct the medicant 34 through the epidermis 16 and into the dermis 18. At process block 208, the method 200 can include moving the medicant 34 into a target volume 42 to interact with tissue, be transported via blood vessels, or a combination thereof. At process block 210, the method 200 can include monitoring the medicant 34 effect. At decision block 218, the method 200 can include determining whether the treatment is complete. If the treatment is determined to be complete by answering yes 222 to decision block 218, then the method 200 can be completed. If the treatment is determined to be incomplete by answering no 220 to decision block 218, then the method 200 can return to process block 202 or can proceed to optional process block 212.

At optional process block 212, the method 200 can include directing a therapeutic acoustic energy field 40 into the target volume 42. When the medicant is located in or near the target volume 42, at optional process block 214, the method 200 can include directing a third acoustic energy field 40 into the target volume 42 to activate the medicant 34.

In certain aspects, the systems and methods disclosed herein can utilize an anesthetic coupled with a non-anesthetic medicant, where the anesthetic can reduce pain and inflammation associated with application of the ultrasound energy, including pain and inflammation associated with the transdermal delivery of the medicant or other ultrasound-generated effects described herein.

In certain aspects, the medicant can be at least partially transparent to ultrasound energy. In certain aspects, the medicant can be substantially transparent to ultrasound energy.

In certain aspects, the stratum corneum layer 14 can be substantially intact prior to the application of ultrasound energy. For example, prior to the application of ultrasound energy, the stratum corneum layer 14 can have no punctures, microchannels, wounds, other means of improving permeability of a medicant, or combinations thereof.

The medicant can be mixed into or be a component of an acoustic coupling medium. In some embodiments, an acoustic coupling medium, such as an acoustic coupling gel or an acoustic coupling cream, can comprise the medicant. In some embodiments, a medicant is administered to a skin surface above the ROI. In some applications, the medicant can be the acoustic coupling medium. In some applications, the medicant can be a combination of medicants, such as any combination of those described herein.

The medicant can be mixed into or can be a component of a biocompatible carrier. Example of a biocompatible medicant carrier include, but are not limited to, glycerin, liposomes, nanoparticles, microbubbles, and the like. In certain aspects, the carrier can enhance and/or lower the threshold for inertial cavitation.

A medicant can comprise an anesthetic. In some aspects, the anesthetic can comprise lidocaine, benzocaine, prilocaine, tetracaine, novocain, butamben, dibucaine, oxybuprocaine, pramoxine, proparacaine, proxymetacaine, tetracaine, or any combination thereof. The anesthetic an eliminate or reduce the pain generated by the application of ultrasound energy to the skin, for example, the creation of the microchannels in the skin by ultrasound energy. The anesthetic can constrict blood flow, which can eliminate or reduce any blood flowing that emerges to the skin surface by way of damage from the application of ultrasound energy to the skin, for example, blood flowing up a microchannel generated by ultrasound energy and onto the skin surface. Further, the use of an anesthetic, such as lidocaine, in the acoustic coupling medium substantially eliminates skin irritation from the application of ultrasound energy, such as the ultrasound-induced creation of microchannels penetrating the skin surface.

A medicant can comprise a drug, a vaccine, a nutraceatical, or an active ingredient. A medicant can comprise blood or a blood component, an allergenic, a somatic cell, a recombinant therapeutic protein, or any living cells that are used as therapeutics to treat diseases or as actives to produce a cosmetic or a medical effect. A medicant can comprise a biologic, such as for example a recombinant DNA therapy, synthetic growth hormone, monoclonal antibodies, or receptor constructs. A medicant can comprise stem cells.

A medicant can comprise adsorbent chemicals, such as zeolites, and other hemostatic agents are used in sealing severe injuries quickly. A medicant can comprise thrombin and/or fibrin glue, which can be used surgically to treat bleeding and to thrombose aneurysms. A medicant can comprise Desmopressin, which can be used to improve platelet function by activating arginine vasopressin receptor 1A. A medicant can comprise a coagulation factor concentrates, which can be used to treat hemophilia, to reverse the effects of anticoagulants, and to treat bleeding in patients with impaired coagulation factor synthesis or increased consumption. A medicant can comprise a Prothrombin complex concentrate, cryoprecipitate and fresh frozen plasma, which can be used as coagulation factor products. A medicant can comprise recombinant activated human factor VII, which can be used in the treatment of major bleeding. A medicant can comprise tranexamic acid and/or aminocaproic acid, which can inhibit fibrinolysis, and lead to a de facto reduced bleeding rate. A medicant can comprise platelet-rich plasma (PRP), mesenchymal stem cells, or growth factors. For example, PRP is typically a fraction of blood that has been centrifuged. The PRP is then used for stimulating healing of the injury. The PRP typically contains thrombocytes (platelets) and cytokines (growth factors). The PRP may also contain thrombin and may contain fibenogen, which when combined can form fibrin glue.

In addition, a medicant can comprise a steroid, such as, for example, like the glucocorticoid cortisol. A medicant can comprise an active compound, such as, for example, alpha lipoic Acid, DMAE, vitamin C ester, tocotrienols, and/or phospholipids. A medicant can comprise a pharmaceutical compound such as for example, cortisone, Etanercept, Abatacept, Adalimumab, or Infliximab. A medicant can comprise Botox. A medicant can comprise lignin peroxidase, which can be derived from fungus and can be used for skin lightening applications. A medicant can comprise hydrogen peroxide, which can be used for skin lighting applications.

The medicant can comprise an anti-inflammatory agent, such as, for example, a non-steroidal anti-inflammatory drug (NSAID), such as aspirin, celecoxib (Celebrex), diclofenac (Voltaren), diflunisal (Dolobid), etodolac (Lodine), ibuprofen (Motrin), indomethacin (Indocin), ketoprofen (Orudis), ketorolac (Toradol), nabumetone (Relafen), naproxen (Aleve, Naprosyn), oxaprozin (Daypro), piroxicam (Feldene), salsalate (Amigesic), sulindac (Clinoril), or tolmetin (Tolectin).

Still further, a medicant can comprise an active ingredient which provides a cosmetic and/or therapeutic effect to the area of application on the skin. Such active ingredients can include skin lightening agents, anti-acne agents, emollients, non-steroidal anti-inflammatory agents, topical anesthetics, artificial tanning agents, antiseptics, anti-microbial and anti-fungal actives, skin soothing agents, sunscreen agents, skin barrier repair agents, anti-wrinkle agents, anti-skin atrophy actives, lipids, sebum inhibitors, sebum inhibitors, skin sensates, protease inhibitors, skin tightening agents, anti-itch agents, hair growth inhibitors, desquamation enzyme enhancers, anti-glycation agents, compounds which stimulate collagen production, and mixtures thereof.

Other examples of such active ingredients can include any of panthenol, tocopheryl nicotinate, benzoyl peroxide, 3-hydroxy benzoic acid, flavonoids (e.g., flavanone, chalcone), farnesol, phytantriol, glycolic acid, lactic acid, 4-hydroxy benzoic acid, acetyl salicylic acid, 2-hydroxybutanoic acid, 2-hydroxypentanoic acid, 2-hydroxyhexanoic acid, cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate), azelaic acid, arachidonic acid, tetracycline, hydrocortisone, acetominophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline, and mixtures thereof.

A medicant can be any natural or synthetic compound or any combination of compounds, or a drug, or a biologic, as described herein, or is known to one skilled in the art, or is developed in the future.

A medicant can be diluted with an appropriate solvent for delivery. For example, a medicant can be diluted or mixed with a solvent to lower viscosity to improve transfer of the medicant. For example, a medicant can be diluted or mixed with a solvent that is a vehicle for transfer of the medicant, such as, for example, mixing a medicant with a formulation of polyethylene glycol (PEG). In some applications, the medicant can be mixed with a solvent to improve a tissue effect, such as uptake into the tissue, such as, for example, mixing a medicant with dimethyl sulfoxide (DMSO). In some applications, the medicant can be mixed with a solvent, which can restrict or inhibit an ultrasound energy effect. For example, a medicant can be mixed with ethanol (EtOH), which inhibits the thermal effect of ablation. In some applications, the medicant can be mixed with a solvent, which can amplify an ultrasound energy effect. For example, a medicant can be mixed with a contrast agent, which can be configured to promote higher attenuation and/or cavitation at lower acoustic pressures.

A medicant can be in a non-liquid state. In some applications, a medicant can be a gel or a solid, which by using a thermal effect, can melt into a liquid state suitable for delivery. For example, a medicant can be mixed into a thermally responsive hydrogel, which is configured to transform into an injectable state upon receiving a suitable amount of thermal energy emitted from a transducer.

In some aspects, a medicant can be administered to a skin surface above the ROI. The medicant can be mixed into or be a component of an acoustic coupling medium. In some applications, the medicant can be the acoustic coupling medium. In some aspects, the acoustic coupling medium can comprise a preservative and/or a preservative enhancer, such as, for example, water-soluble or solubilizable preservatives including Germall 115, methyl, ethyl, propyl and butyl esters of hydroxybenzoic acid, benzyl alcohol, sodium metabisulfite, imidazolidinyl urea, EDTA and its salts, Bronopol (2-bromo-2-nitropropane-1,3-diol) and phenoxypropanol; antifoaming agents; binders; biological additives; bulking agents; coloring agents; perfumes, essential oils, and other natural extracts.

In certain aspects, microchannels 60 can be long enough for fluid communication between the skin surface 12 and the epidermis 16. The microchannels 60 can have a diameter large enough to allow the medicant to pass from the skin surface 12 to the epidermis 16. The microchannels 60 can have a diameter small enough to prevent bleeding from subcutaneous tissue to the skin surface 12.

In certain aspects, a single ultrasound pulse can provide sufficient effect to drive the medicant through the stratum corneum 14. In some aspects, two more ultrasound pulses, including but not limited to, two, three, four, five, six, seven, eight, nine, ten, or more ultrasound pulses can provide sufficient effect to drive the medicant through the stratum corneum 14.

In certain aspects, the systems and methods described herein can drive medicant through the stratum corneum 14 after application of ultrasound energy for a total length of time of less than 5 minutes, including but not limited to, less than 3 minutes, less than 1 minute, less than 50 seconds, less than 40 seconds, less than 30 seconds, less than 25 seconds, less than 20 seconds, less than 15 seconds, less than 10 seconds, less than 5 seconds, less than 4 seconds, less than 3 seconds, less than 2 seconds, or less than 1 second.

The systems and methods described herein can be employed in numerous clinical applications. For example, a treatment for scars can include a medicant directed by acoustic energy through microchannels to a scar location. A second acoustic energy can be directed to the scar location and be configured to interact with the medicant to remodel and/or modify the scar tissue and eventually replace the scar tissue via remodeling. The treatment can also include directing therapeutic acoustic energy into the scar tissue. In some applications, the therapeutic acoustic energy can be configured to ablate a portion of the scar tissue, thereby removing a portion of the scar tissue. In some applications, the therapeutic acoustic energy can be configured to create a lesion in or near the scar tissue, thereby facilitating skin tightening above the lesion. In some applications, the therapeutic acoustic energy can be configured to remodel and/or increase an amount of collagen around the scar tissue, thereby replacing portions of the scar tissue with newly formed collagen.

In another example, the systems and methods described herein can be used in the treatment of hyperpigmentation. A medicant can be a skin lightening agent, which can be any active ingredient that improves hyperpigmentation. Without being bound by theory, use of skin lightening agents can effectively stimulate the epidermis, particularly the melanocyte region, where the melanin is generated. The combined use of the skin lightening agent and ultrasound energy can provide synergistic skin lightening benefit. A medicant comprise a skin lightening agent, such as, for example, ascorbic acid compounds, vitamin B3 compounds, azelaic acid, butyl hydroxyanisole, gallic acid and its derivatives, glycyrrhizinic acid, hydroquinone, kojic acid, arbutin, mulberry extract, and mixtures thereof. Use of combinations of skin lightening agents can be advantageous as they may provide skin lightening benefit through different mechanisms.

In one aspect, a combination of ascorbic acid compounds and vitamin B3 compounds can be used. Examples of ascorbic acid compounds can include L-ascorbic acid, ascorbic acid salt, and derivatives thereof. Examples of ascorbic acid salts include sodium, potassium, lithium, calcium, magnesium, barium, ammonium and protamine salts. Examples of ascorbic acid derivatives include for example, esters of ascorbic acid, and ester salts of ascorbic acid. Examples of ascorbic acid compounds include 2-O-D-glucopyranosyl-L-ascorbic acid, which is an ester of ascorbic acid and glucose and usually referred to as L-ascorbic acid 2-glucoside or ascorbyl glucoside, and its metal salts, and L-ascorbic acid phosphate ester salts such as sodium ascorbyl phosphate, potassium ascorbyl phosphate, magnesium ascorbyl phosphate, and calcium ascorbyl phosphate. In addition, medicant can comprise lignin peroxidase, which can be derived from fungus used for skin lightening applications. In another example, medicant can comprise hydrogen peroxide, which can be used for skin lighting applications.

In an exemplary application, a coupling agent can comprise a medicant, which comprises a skin lighting agent. Ultrasound energy can direct the lightening agent into the epidermis and into contact with melanin. The lightening agent can remove excess melanin. Additional ultrasound energy can be directed to the epidermis to provide a cavitation effect to break up the excess melanin pigment. In some examples, additional ultrasound energy can be directed to the epidermis to provide a thermal effect, which can be configured to increase the effectiveness of the skin lightening agent. In one example, the skin lightening agent can be hydrogen peroxide and the ultrasound energy can increase the temperature of the hydrogen peroxide by at least 1° C. and to about 15° C., which increases the effectiveness of the skin lightening agent.

In another example of a clinical application, the systems and methods described herein can be used in the treatment of hypopigmentation. In an exemplary application, a coupling agent can comprise a medicant, which can comprise a corticosteroid. Ultrasound energy can direct the corticosteroid into the epidermis at the light colored areas of the skin. A second ultrasound energy can be directed to the treatment location and be configured to interact with the corticosteroid to provide a synergistic treatment to increase pigment concentration at the treatment location. A second energy, such as, a photon-based energy from a laser can be directed to the treatment location to further increase the pigment concentration in the treatment location. A third energy, such as, ultrasound energy can be directed to the treatment location to disperse the generated pigment and provide an even coloring pattern at the treatment location.

In another example, large molecule medicants can be delivered using the systems and methods described herein. A large molecule can be greater than 500 Da. A large molecule can be any medicinal product manufactured in or extracted from biological sources. Examples of large molecule include vaccines, blood or blood components, allergenics, somatic cells, gene therapies, tissues, recombinant therapeutic protein and living cells. In one example, a large molecule comprises stem cells. An energy effect is provided by an acoustic energy field, which is configured to drive the large molecule through the microchannels and into subcutaneous tissue. The energy effect can be acoustic streaming and/or inertial cavitation. In some applications, the energy effect is a thermal effect, which can be configured to lower the viscosity of a large molecule for improved transfer through the microchannels.

In another example, chemotherapy drugs can be delivered using the systems and methods described herein. Some of the advantages, of using such systems and methods, include concentrating the chemotherapy drug to the tumor site (as opposed to exposing the whole body to the drug), lower doses may be required (due to the site specific treatment), and greater effectiveness of the drug.

In some applications, a chemotherapy drug can be a large molecule. In some applications, the systems and methods, described herein, can deliver anti-body drug conjugates, which target cancer stem cells to destroy a tumor. In some applications, a chemotherapy drug is a liposome encapsulated chemotherapy drug, which can be delivered through the microchannels to a treatment site by an acoustic energy field, and then a second acoustic energy field can be delivered to melt the liposome and release the chemotherapy drug. In some applications, an acoustic energy field can be delivered, which is configured to provide microbubbles (cavitation) to a tumor in a treatment site without generating heat, which can lead to reduction or elimination of the tumor. These microbubbles can increase microvessel permeability of drugs, enhance drug penetration through the interstitial space, and increase tumor cell uptake of the drugs, thus enhancing the antitumor effectiveness of the drugs.

In some applications of chemotherapy, a drug-loaded nanoemulsion can be driven through the microchannels to a tumor site via an acoustic energy field. A second acoustic energy field can be delivered to the tumor site and can be configured to trigger drug release from nanodroplets, which can be created by microbubbles. A third acoustic energy field can be delivered to the tumor site and can be configured to produce an energy effect, for example, a thermal effect and/or cavitation, which enhances uptake of the drug by the tumor.

In another example, photodynamic therapy can be delivered using the systems and methods described herein. As known to one skilled in the art, photodynamic therapy is a medical treatment that utilizes a medicant, which comprises a photosensitizing agent and a photon-emission source to activate the administered medicant. In some applications, the medicant comprising a photosensitizing agent is delivered through the microchannels into tissue via an acoustic energy field. After the medicant has been delivered, a second acoustic energy field can be delivered to enhance permeability and/or uptake of the medicant by the tissue. After the medicant has been delivered, a photon energy field at a specific wavelength is delivered from the photon-emission source to the tissue, which activates the medicant. The photon-emission source can include, but are not limited to: laser, LED or intense pulsed light. The optimal photon-emission source is determined by the ideal wavelength for activation of the medicant and the location of the target tissue. The photon energy field is directly applied to the target tissue for a specific amount of time. The medicant can be Levulan, which is used for the treatment of skin cancer. The medicant can be Metvix, which is used for the treatment of skin cancer. The medicant can be Photofin, which is used for the treatment of bladder cancer, lung cancer and esophagus cancer. The medicant can be aminolevulinic acid, which has been used in the treatment of various skin conditions, such as, for example, acne, rosacea, sun damage, enlarged sebaceous glands, wrinkles, warts, hidradenitis suppurativa, and psoriasis.

In another example, injuries to muscles can be treated using the systems and methods described herein. For treating an injury to a muscle, ligament, or tendon, a medicant can comprise platelet-rich plasma (PRP), mesenchymal stem cells, or growth factors. For example, PRP is typically a fraction of blood that has been centrifuged. The PRP is then used for stimulating healing of the injury. The PRP typically contains thrombocytes (platelets) and cytokines (growth factors). The PRP may also contain thrombin and may contain fibenogen, which when combined can form fibrin glue. The medicant is directed through a microchannels to the injury, such as, for example a tear in the tissue. An acoustic energy field can then be directed to the injury to activate the medicant and/or disperse the medicant. The acoustic energy field can create a thermal effect to heat the injury location which can initiate interaction of the medicant with the tissue at the injury location and/or increase blood perfusion in the injury location. The acoustic energy field can ablate a portion of tissue in the injury location, which can peak inflammation and increase the speed of the healing process. The acoustic energy field can be directed to the injury location and weld together the tear using both an ablative thermal effect and various mechanical effects.

In an example, acne can be treated using the systems and methods described herein. A medicant can comprise any one or more of cis-retinoic acid, trans-retinoic acid, retinol, retinyl esters (e.g., retinyl propionate), phytic acid, N-acetyl-L-cysteine, lipoic acid, tocopherol and its esters (e.g., tocopheryl acetate), azelaic acid, arachidonic acid, tetracycline, ibuprofen, naproxen, ketoprofen, hydrocortisone, acetaminophen, resorcinol, phenoxyethanol, phenoxypropanol, phenoxyisopropanol, 2,4,4'-trichloro-2'-hydroxy diphenyl ether, 3,4,4'-trichlorocarbanilide, octopirox, lidocaine hydrochloride, clotrimazole, miconazole, ketoconazole, neomycin sulfate, theophylline. The medicant is directed through the microchannels to a ROI comprising a sebaceous gland. The medicant interacts with bacteria in the sebaceous gland to reduce or eliminate the bacteria responsible for acne. An acoustic energy field can provide a mechanical effect to disperse the medicant into one or more sebaceous gland. An acoustic energy field can provide a thermal effect to accelerate the reaction of the medicant to eliminate or reduce the amount of bacteria in the sebaceous gland. An acoustic energy field can provide a thermal effect to injure or destroy at least a portion of the sebaceous gland. A photon based energy field can be directed to the medicant in the ROI to initiate a photodymanic effect to activate the medicant. A photon based energy field can be directed to the medicant in the ROI to reduce photosensitivity of the tissue in the ROI from sunlight.

As used herein, pulse width is the time from the start of the pulse to the end of the pulse measured at a −3 dB or −6 dB power point.

As used herein, "acoustic streaming" refers to a force of acoustic energy which displaces a material through a tissue environment.

Example 1

Figure 5A:
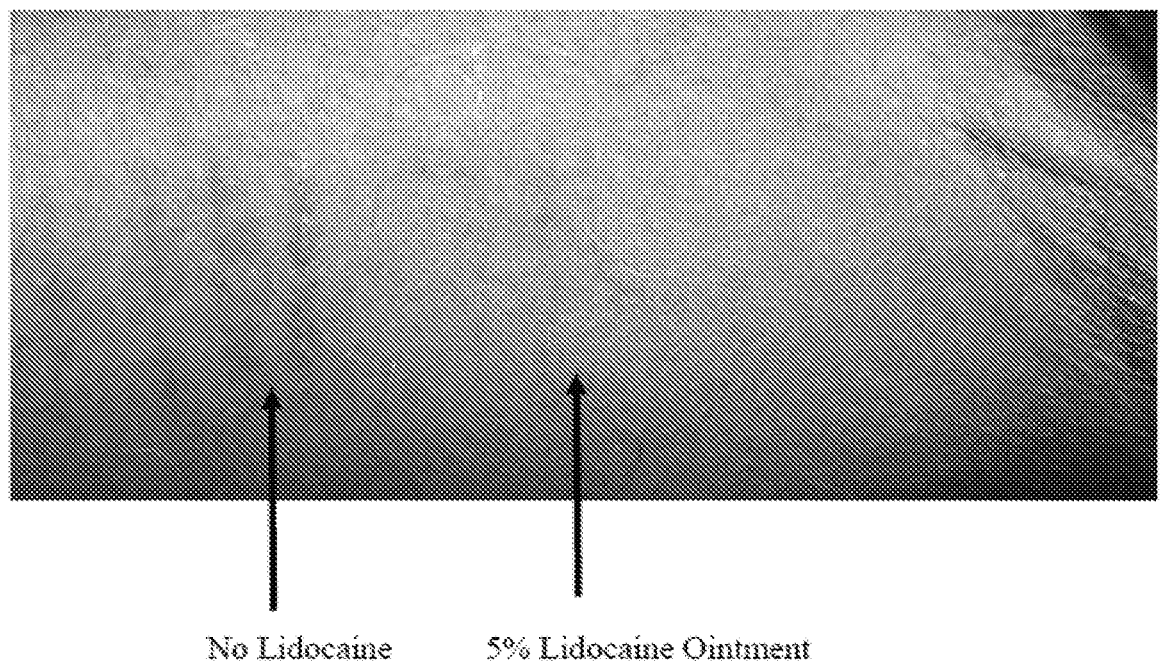
FIG. 5A is a picture showing the result of applying a method according to one aspect of the present disclosure with and without a 5% lidocaine ointment, as shown in Example 1.
Figure 5B:
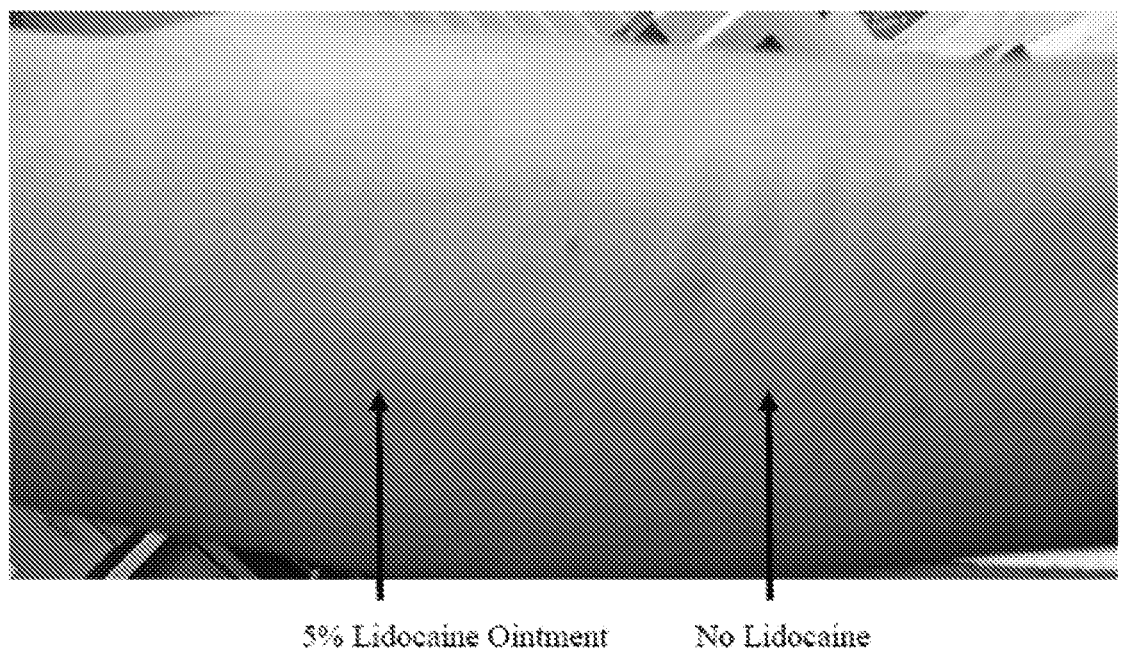
FIG. 5B is a picture showing the result of applying a method according to one aspect of the present disclosure with and without a 5% lidocaine ointment, as shown in Example 1.

An ultrasound transducer was coupled to a forearm of two human patients with a standard acoustic coupling gel in one location and a 5% topical solution of lidocaine as an acoustic coupling gel in a second location. The 5% topical solution of lidocaine had negligible acoustic attenuation of less than 1 dB/cm/MHz. The ultrasound transducer transmitted ultrasound energy at 10 MHz, a pulse width of 25 ms, and an energy of 0.5 J. The ultrasound energy was focused to a depth of 1.5 mm beneath the surface of human skin. The presence of the 5% topical solution of lidocaine reduced pain from the application of the ultrasound energy by approximately 2 points on a 10-point pain scale when compared with the application of the ultrasound energy in the absence of the lidocaine. Referring to FIG. 5A, the ultrasound energy was applied in treatment lines to an area on the left with only the standard acoustic coupling gel present and the same ultrasound energy was applied to an area on the right with the 5% lidocaine solution present on the skin surface. Referring to FIG. 5B, the ultrasound energy was applied in treatment lines to an area on the right with only the standard acoustic coupling gel present and the same ultrasound energy was applied to an area on the left with a 5% lidocaine ointment present on the skin surface. FIGS. SA and SB show evidence of the treatment effect of lidocaine in this disclosure. After the application of the ultrasound energy, the treatment areas that did not have lidocaine applied to them were irritated, red, and welt-like, whereas the treatment areas that did have lidocaine applied to them were smooth and contained barely visible remnants. The ultrasound energy that was utilized exhibited broadband spectral properties when applied to water, gel, and tissue, which is evidence of an inertial cavitation effect.

Example 2

An ultrasound transducer was coupled to an ex-vivo sample of pig skin with dyed water as a coupling agent. The water was dyed with a green food dye. The ultrasound transducer transmitted ultrasound energy in treatment lines of high intensity ultrasound point exposures at a frequency of 2.87 MHz, a pulse width of 170 ms, and a pulse power of 10 W. The ultrasound energy was focused to a depth of approximately 1.5 mm beneath the surface of the pig skin. Locations that were not treated with the ultrasound energy showed penetration of the dye ranging from 1.0 mm to 1.5 mm. Locations that were treated with the ultrasound energy showed penetration of the dye ranging from 2.0 mm to 2.8 mm, thereby showing that the application of the ultrasound energy enhanced the transdermal transport of the water containing the dye. The ultrasound energy that was utilized exhibited broadband spectral properties when applied to water, gel, and tissue, which is evidence of an inertial cavitation effect.

The present disclosure has been described above with reference to various exemplary configurations. However, those skilled in the art will recognize that changes and modifications may be made to the exemplary configurations without departing from the scope of the present invention. For example, the various operational steps, as well as the components for carrying out the operational steps, may be implemented in alternate ways depending upon the particular application or in consideration of any number of cost functions associated with the operation of the system, e.g., various of the steps may be deleted, modified, or combined with other steps. Further, it should be noted that while the method and system for ultrasound treatment as described above is suitable for use by a medical practitioner proximate the patient, the system can also be accessed remotely, i.e., the medical practitioner can view through a remote display having imaging information transmitted in various manners of communication, such as by satellite/wireless or by wired connections such as IP or digital cable networks and the like, and can direct a local practitioner as to the suitable placement for the transducer. Moreover, while the various exemplary embodiments may comprise non-invasive configurations, system can also be configured for at least some level of invasive treatment application. These and other changes or modifications are intended to be included within the scope of the present invention, as set forth in the following claims.

The invention claimed is:

1. A method for ultrasound-assisted delivery of a medicant through a stratum corneum layer of a skin surface, the method comprising:
  a) administering the medicant and an anesthetic to the skin surface;
  b) coupling an ultrasound transducer to the medicant, the anesthetic, and the skin surface; and
  c) generating inertial cavitation in the stratum corneum layer and driving the medicant through the stratum corneum layer by applying a first pulsed acoustic energy field from the ultrasound transducer to the skin surface, the first pulsed acoustic energy field having a frequency from 1 MHz to 30 MHz, a peak intensity from 100 W/cm² to 100 kW/cm² at the skin surface, and a pulse width from 33 nanoseconds to 5 seconds, wherein the inertial cavitation initiates damage in or beneath the skin surface, the anesthetic alleviating pain or swelling associated with the damage in or beneath the skin surface.

2. The method according to claim 1, wherein the first pulsed ultrasound energy has a pulse repetition rate from one pulse per 10 microseconds to one pulse per 100 seconds.

3. The method according to claim 1, wherein the first pulsed acoustic energy field creates a thermal effect in a tissue beneath the stratum corneum layer, thereby raising a temperature of the tissue by 1° C. to 15° C.

4. The method according to claim 1, the method further comprising:
  d) applying a second intermittent pulsed acoustic energy field between pulses of the first pulsed acoustic energy field, the second intermittent pulsed acoustic energy field having a frequency from 1 MHz to 30 MHz, a peak intensity from 5 W/cm² to 100,000 W/cm² at the skin surface, and a pulse width from 1 microsecond to 0.1 seconds, the first pulsed acoustic energy field and the second intermittent pulsed acoustic energy field generating inertial cavitation in the stratum corneum layer and driving the medicant through the stratum corneum layer.

5. The method according to claim 1, the method further comprising:
  d) focusing a second pulsed acoustic energy field to a target volume at a depth beneath the stratum corneum layer, the second acoustic energy field configured to generate a thermal effect in the target volume, thereby ablating at least a portion of the target volume.

6. The method according to claim 5, wherein the thermal effect raises a temperature in the target volume by 15° C. to 65° C. without damaging an intervening tissue between the skin surface and the target volume.

7. The method according to claim 1, the method further comprising:
  d) applying a second pulsed acoustic energy field focused to a depth beneath the skin surface, wherein the second pulsed acoustic energy field is emitted from the ultrasound transducer or a different ultrasound transducer, the second pulsed acoustic energy field having a frequency from 1 MHz to 30 MHz, an intensity from 5 W/cm² to 70,000 W/cm², and a pulse width from 33 nanoseconds to 1 second, thereby creating acoustic streaming having a pressure from 10 kPa to 100 MPa and driving the medicant through an epidermis layer and into a dermis layer.

8. The method according to claim 7, wherein the first pulsed acoustic energy field or the second pulsed acoustic energy field creates a thermal effect in the epidermis layer or the dermis layer, the thermal effect elevating a temperature by 1° C. to 15° C.

9. The method according to claim 8, wherein the thermal effect increases blood perfusion within the epidermis layer or the dermis layer, thereby increasing absorption of the medicant into a bloodstream.

10. The method according to claim 1, the method further comprising:
  d) applying a second pulsed acoustic energy field configured to provide an inertial cavitation effect at a depth of 0.5 millimeter to 7 millimeters beneath the skin surface, the second pulsed acoustic energy field having a frequency from 1 MHz to 30 MHz, a peak intensity from 3 W/cm² to 100 kW/cm², and a pulse width from 33 nanoseconds to 100 seconds, thereby increasing dispersion of the medicant in an epidermis layer or a dermis layer beneath the skin surface.

11. A method for ultrasound-assisted delivery of a medicant through a stratum corneum layer of a skin surface, the method comprising:
  a) contacting a skin surface with a coupling medium comprising a medicant, the skin surface including a stratum corneum layer;
  b) coupling an ultrasound transducer to the medicant and the skin surface; and
  c) generating inertial cavitation in the stratum corneum layer and driving the medicant through the stratum corneum layer by applying a first pulsed acoustic energy field from the ultrasound transducer to the skin surface, the first pulsed acoustic energy field having a frequency from 1 MHz to 30 MHz, a peak intensity from 100 W/cm² to 100 kW/cm² at the skin surface, and a pulse width from 33 nanoseconds to 5 seconds, wherein the inertial cavitation initiates damage in or beneath the skin surface.

* * * * *